(12) United States Patent
Kovalsky

(10) Patent No.: US 8,926,690 B2
(45) Date of Patent: Jan. 6, 2015

(54) HEART VALVE PROSTHESIS

(71) Applicant: Medtronic, Inc., Minneapolis, MN (US)

(72) Inventor: Igor Kovalsky, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/795,101

(22) Filed: Mar. 12, 2013

(65) Prior Publication Data

US 2014/0046426 A1   Feb. 13, 2014

Related U.S. Application Data

(63) Continuation-in-part of application No. 13/572,842, filed on Aug. 13, 2012.

(51) Int. Cl.
*A61F 2/06* (2013.01)
*A61F 2/24* (2006.01)

(52) U.S. Cl.
CPC ............. *A61F 2/2475* (2013.01); *A61F 2/2436* (2013.01); *A61F 2/2412* (2013.01); *A61F 2/2418* (2013.01); *A61F 2/2409* (2013.01)
USPC ............................ 623/1.26; 623/1.24; 623/2.1

(58) Field of Classification Search
USPC ........................................ 623/1.26, 1.24, 2.1
See application file for complete search history.

(56) References Cited

U.S. PATENT DOCUMENTS

| | | | |
|---|---|---|---|
| 5,957,949 | A | 9/1999 | Leonhardt |
| 7,748,389 | B2 | 7/2010 | Salahieh et al. |
| 7,947,075 | B2 | 5/2011 | Goetz et al. |
| 2003/0036791 | A1 | 2/2003 | Philipp et al. |
| 2003/0199963 | A1 | 10/2003 | Tower et al. |
| 2003/0199971 | A1 | 10/2003 | Tower et al. |
| 2004/0111111 | A1 | 6/2004 | Lin |
| 2008/0071361 | A1 | 3/2008 | Tuval et al. |
| 2009/0216313 | A1 | 8/2009 | Straubinger et al. |
| 2009/0240320 | A1 | 9/2009 | Tuval et al. |
| 2009/0276027 | A1 | 11/2009 | Glynn |

(Continued)

FOREIGN PATENT DOCUMENTS

| | | |
|---|---|---|
| CA | 2827556 | 7/2012 |
| WO | WO/2004/019825 | 3/2004 |

(Continued)

OTHER PUBLICATIONS

Boudjemline et al. "Steps Toward Percutaneous Aortic Valve Replacement" Circulation 2002; 105; 775-558.

(Continued)

*Primary Examiner* — Thomas J Sweet
*Assistant Examiner* — Matthew Schall

(57) ABSTRACT

A heart valve prosthesis configured for deployment within a native heart valve. The heart valve prosthesis includes a tubular stent and a prosthetic valve component disposed within and secured to the stent. In addition, one or more elements are coupled to a distal end of the stent to position, anchor, and/or seal the prosthesis within the native heart valve. Each element transforms from a compressed configuration in which the elements distally extend from the distal end of the stent to a deployed configuration in which the elements proximally extend from the distal end of the stent. Each element includes at least one U-shaped or V-shaped support arm that bends radially outward and then towards an outer surface of the stent such that it translates more than ninety degrees from the compressed configuration. Each element may include an outer support arm and an inner support arm.

20 Claims, 24 Drawing Sheets

(56) References Cited

U.S. PATENT DOCUMENTS

| | | |
|---|---|---|
| 2010/0191320 A1 | 7/2010 | Straubinger et al. |
| 2010/0262231 A1 | 10/2010 | Tuval et al. |
| 2011/0137397 A1 | 6/2011 | Chau et al. |
| 2012/0041550 A1 | 2/2012 | Salahieh et al. |
| 2012/0078360 A1 | 3/2012 | Rafiee |
| 2012/0101572 A1 | 4/2012 | Kovalsky et al. |

FOREIGN PATENT DOCUMENTS

| | | |
|---|---|---|
| WO | WO2012/095159 | 7/2012 |
| WO | WO 2013/021374 | 2/2013 |
| WO | WO2014/028112 | 2/2014 |

OTHER PUBLICATIONS

Lauten et al., "Experimental Evaluation of the JenaClip Transcatheter Aortic Valve" Catheterization and Cardiovascular Interventions 74:514-519 (2009).

Chau, Mark, U.S. Appl. No. 61/287,099, "Prosthetic Mitral Valve With Subvalvular Anchoring" filed Dec. 16, 2009.

Chau et al. U.S. Appl. No. 61/266,774, "Prosthetic Mitral Valve with Subvalvular Anchoring" filed Dec. 4, 2009.

International Search Report and Written Opinion, Int'l Appl. No. PCT/US2013/045789, Dated Dec. 6, 2013.

PCT/US2014/020876, PCT International Search Report and Written Opinion, mailed Jul. 2, 2014.

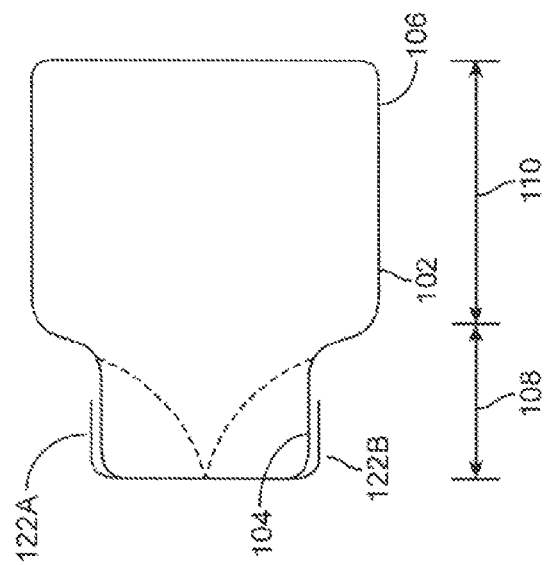
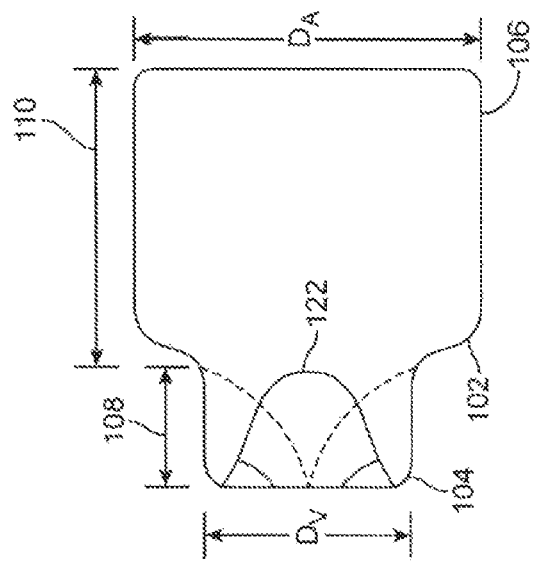
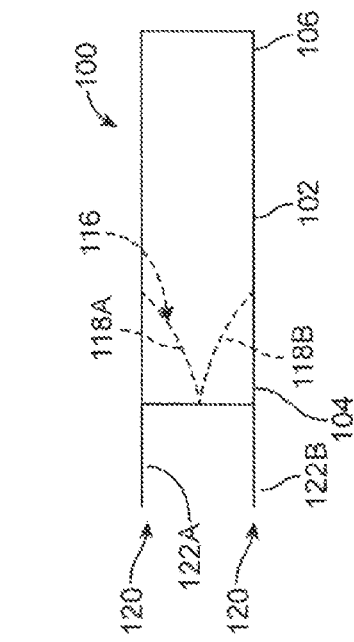
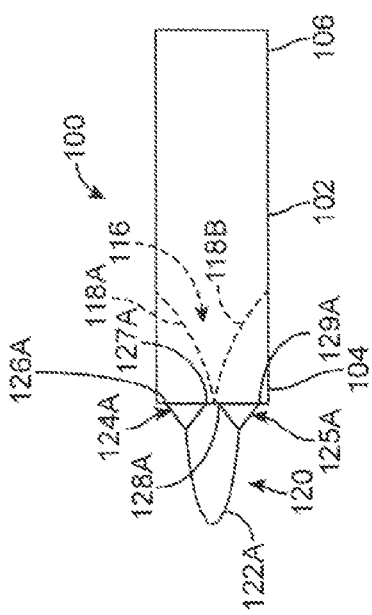

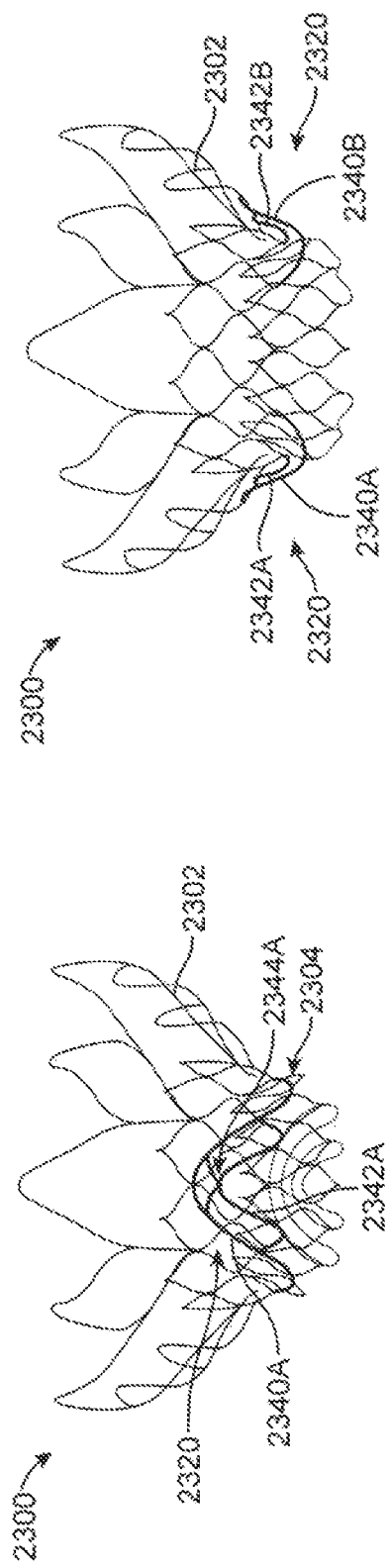
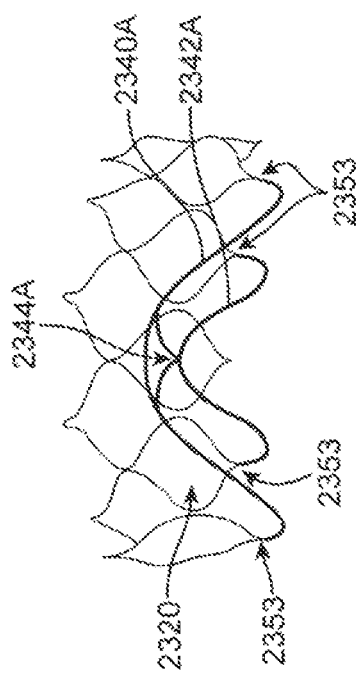
FIG. 23A
FIG. 23B
FIG. 23C

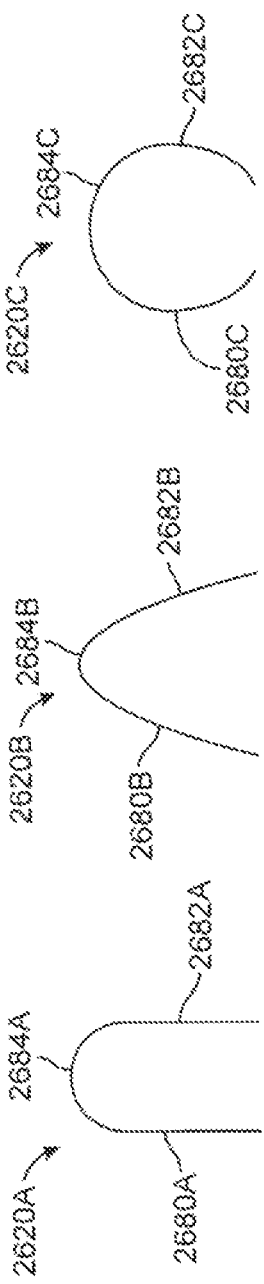
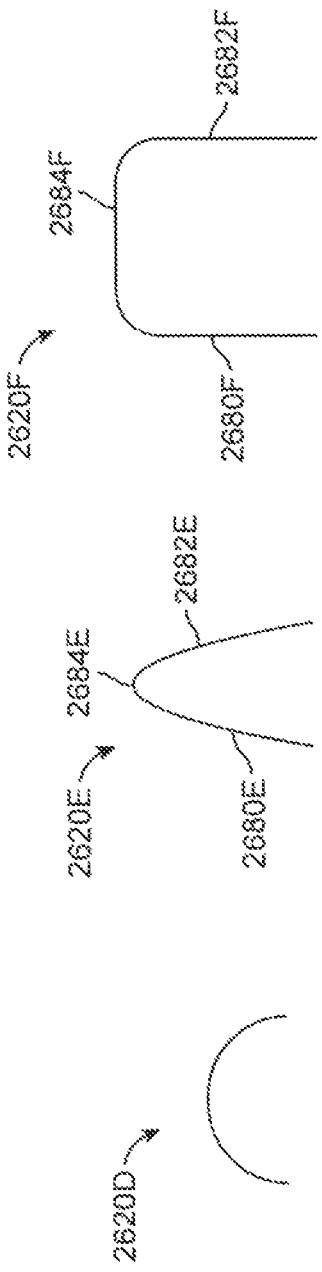

HEART VALVE PROSTHESIS

RELATED APPLICATIONS

This application is a Continuation-in-Part of and claims the benefit of U.S. patent application Ser. No. 13/572,842 filed Aug. 13, 2012. The disclosures of which are herein incorporated by reference in their entirety.

FIELD OF THE INVENTION

The present invention is directed to a valve prosthesis having elements for sealing, positioning and/or anchoring the prosthesis at a target location and a method of percutaneously delivering the prosthesis to the target location.

BACKGROUND OF THE INVENTION

A wide range of medical treatments are known that utilize "endoluminal prostheses." As used herein, endoluminal prostheses are intended to mean medical devices that are adapted for temporary or permanent implantation within a body lumen, including both naturally occurring and artificially made lumens. Examples of lumens in which endoluminal prostheses may be implanted include, without limitation: arteries, veins gastrointestinal tract, biliary tract, urethra, trachea, hepatic and cerebral shunts, and fallopian tubes. Stent prostheses are known for implantation within a body lumen for providing artificial radial support to the wall tissue that defines the body lumen. To provide radial support to a blood vessel, such as one that has been widened by a percutaneous transluminal coronary angioplasty, commonly referred to as "angioplasty," "PTA" or "PTCA", a stent may be implanted in conjunction with the procedure. Under this procedure, the stent may be collapsed to an insertion diameter and inserted into the vasculature at a site remote from the diseased vessel. The stent may then be delivered to the desired treatment site within the affected vessel and deployed, by self-expansion or radial expansion, to its desired diameter for treatment.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower, et al., each of which is incorporated by reference herein in its entirety. Minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state.

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which the opening of a valve is narrowed or in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

The two atrio-ventricular valves through which blood flows from the atria to the ventricles function to prevent return of blood to the atrium. The tricuspid valve, also known as the right atrioventricular valve, is a tri-flap valve located between the right atrium and the right ventricle. The mitral valve, also known as the bicuspid or left atrioventricular valve, is a dual-flap valve located between the left atrium (LA) and the left ventricle (LV), and serves to direct oxygenated blood from the lungs through the left side of the heart and into the aorta for distribution to the body. As with other valves of the heart, the mitral valve is a passive structure in that it does not itself expend any energy and does not perform any active contractile function. The mitral valve includes two moveable leaflets that each open and close in response to differential pressures on either side of the valve. Ideally, the leaflets move apart from each other when the valve is in an open position, and meet or "coapt" when the valve is in a closed position. Problems that may develop with mitral valves include stenosis in which the mitral valve does not open properly, and/or insufficiency or regurgitation in which the mitral valve does not close properly. Stenosis and insufficiency may occur concomitantly in the same valve. The effects of valvular dysfunction vary, with mitral regurgitation or backflow typically having relatively severe physiological consequences to the patient.

Due to the different physical characteristics of the mitral valve as compared to other valves such as the pulmonary valve, percutaneous implantation of a valve in the mitral position has its own unique requirements for valve replacement. There is a continued desire to improve mitral valve replacement devices and procedures to accommodate the structure of the heart, including by providing improved devices and methods for replacing the mitral valve percutaneously.

Various transcatheter delivery methods may provide safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state within the native valve. Calcified or diseased native leaflets may be pressed to the side walls of the native valve by the radial force of the stent frame of the prosthetic valve. These calcified leaflets do not allow complete conformance of the stent frame with the native valve and can be a source of paravalvular leakage (PVL). Significant pressure gradients across the valve cause blood to leak through the gaps between the implanted prosthetic valve and the calcified anatomy. Therefore, there is a desire to improve heart valve replacement devices and procedures to minimize or prevent PVL from occurring.

BRIEF SUMMARY OF THE INVENTION

Embodiments hereof relate to a heart valve prosthesis that includes a tubular stent or frame and a prosthetic valve component disposed within and secured to the stent. The stent or frame has a compressed configuration for delivery within a vasculature and a deployed configuration for deployment within a native heart valve. In one embodiment, one or more elements for positioning are coupled to a distal end or a proximal end of the stent to position and anchor the prosthesis within the native heart valve. In an alternative embodiment, one or more elements for sealing are coupled to a distal end or a proximal end of the stent to seal the prosthesis within the native heart valve. In one embodiment, each element for positioning and/or sealing includes an outer U-shaped or V-shaped support arm and an inner U-shaped or V-shaped support arm that either distally extend from the distal end of the stent or proximally extend from the proximal end of the stent when the stent is in the compressed configuration. During deployment of the prosthesis, each support arm bends radially outward and then towards an outer surface of the stent such that it translates more than ninety degrees from the compressed configuration to either proximally extend from the distal end of the stent or to distally extend from the proximal end of the stent when the stent is in the deployed configuration.

According to another embodiment hereof, a heart valve prosthesis includes a tubular stent or frame and a prosthetic valve component disposed within and secured to the stent. The stent or frame has a compressed configuration for delivery within a vasculature and a deployed configuration for deployment within a native heart valve. In one embodiment, one or more elements for positioning are coupled to a distal end or a proximal end of the stent to position and anchor the prosthesis within the native heart valve. In an alternative embodiment, one or more elements for sealing are coupled to a distal end or a proximal end of the stent to seal the prosthesis within the native heart valve. In one embodiment, each element for positioning and/or sealing is attached to the stent by two V-shaped connectors such that there are four connection points between each positioning and/or sealing element and the stent. Each positioning and/or sealing element includes a U-shaped or V-shaped support arm that is approximately parallel with a longitudinal axis of the stent and either distally extends from the distal end of the stent when the stent is in the compressed configuration or proximally extends from the proximal end of the stent when the stent is in the compressed configuration. During deployment of the prosthesis, each element for positioning and/or sealing bends radially outward and then towards an outer surface of the stent such that the support arm translates between 135 degrees and 180 degrees from the compressed configuration to either proximally extend from the distal end of the stent or to distally extend from the proximal end of the stent when the stent is in the deployed configuration.

Some embodiments hereof also relate to a method of percutaneously delivering and deploying a prosthetic valve within a native valve, for example, a mitral valve or an aortic valve. A prosthetic valve delivery system is tracked through the vasculature to the native valve. The prosthetic valve delivery system includes a valve prosthesis having a tubular stent, a prosthetic valve component disposed within and secured to the stent, and one or more elements for positioning and/or sealing coupled to a distal end of the stent and/or a proximal end of the stent, the positioning and/or sealing elements each having an outer U-shaped or V-shaped support arm and an inner U-shaped or V-shaped support arm that distally extend from the distal end of the stent when the stent is in a compressed configuration for delivery and/or proximally extend from the proximal end of the stent when the stent is in a compressed configuration for delivery. An outer sheath of the prosthetic valve delivery system is retracted to expose the positioning and/or sealing elements, wherein each support arm bends radially outward and then towards an outer surface of the stent such that it translates more than ninety degrees from the compressed configuration to either proximally extend from the distal end of the stent or distally extend from the proximal end of the stent and press against the native valve and/or the ventricular wall in order to position and/or seal the valve prosthesis. The outer sheath is further retracted to expose the stent, thereby allowing the stent to self-expand into a deployed configuration.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1A and FIG. 1B are schematic side and top views, respectively, of a valve prosthesis having elements for positioning and/or sealing according to an embodiment hereof, wherein the valve prosthesis is in a delivery or compressed configuration with elements for positioning and/or sealing distally extending from a distal end of the prosthesis.

FIG. 2A and FIG. 2B are schematic side and top views, respectively, of the valve prosthesis of FIG. 1A and FIG. 1B, wherein the valve prosthesis is in an expanded or deployed configuration with elements for positioning and/or sealing proximally extending from a distal end of the prosthesis.

FIGS. 23A and 23B illustrate two side views of a valve prosthesis having elements for positioning and/or sealing with outer and inner U-shaped support arms according to an embodiment hereof, wherein the support arms extend from distalmost crowns of the valve prosthesis and the valve prosthesis is in an expanded or deployed configuration.

FIG. 23C is an enlarged view of a portion of the valve prosthesis of FIG. 23A.

FIGS. 26A-26F illustrates various configurations of generally U-shaped or V-shaped support arms according to embodiments hereof.

DETAILED DESCRIPTION OF THE INVENTION

Figure 3:
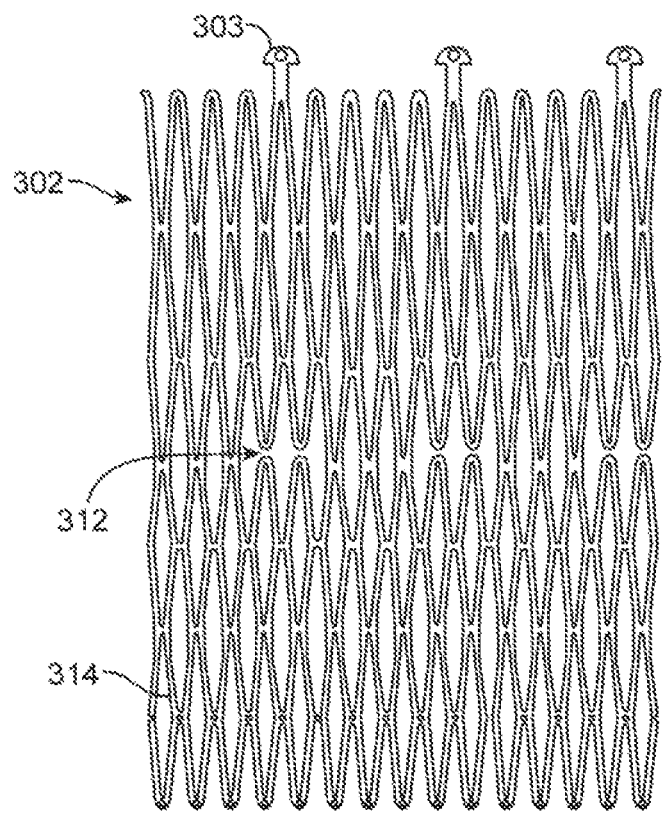
FIG. 3 is a side view illustration of an exemplary stent that may be utilized in the valve prosthesis of FIG. 1A and FIG. 1B, wherein the stent is in a delivery or compressed configuration.
Figure 4:
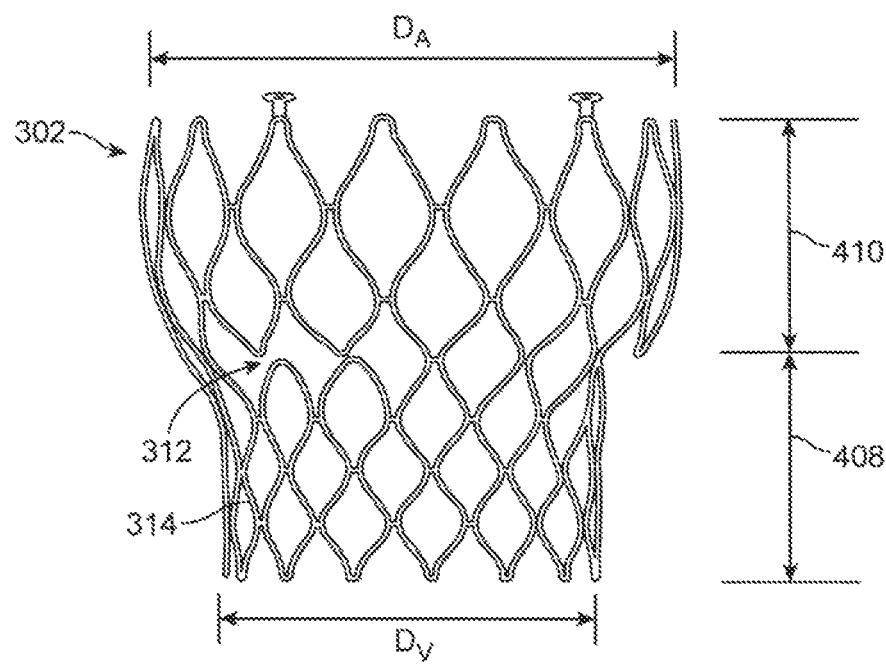
FIG. 4 is a side view illustration of the exemplary stent of FIG. 3, wherein the stent is in an expanded or deployed configuration.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, as used herein, the terms "outward" or "outwardly" refer to a position radially away from a longitudinal axis of the stent and the terms "backward" or "backwardly" refer to the relative transition from a proximal position to a distal position.

The following detailed description is merely exemplary in nature and is not intended to limit the invention or the application and uses of the invention. Although the description of the invention is in the context of treatment of heart valves such as the mitral valve or aortic valve, the invention may also be used in any other body passageways where it is deemed useful. For example, the present invention may be applied to venous valves as well. Furthermore, there is no intention to be bound by any expressed or implied theory presented in the preceding technical field, background, brief summary or the following detailed description.

Some embodiments hereof are related to a valve prosthesis configured for placement at a mitral valve in the heart that lies between the left atrium (LA) and the left ventricle (LV). Some embodiments hereof are related to a valve prosthesis configured for placement at an aortic valve in the heart that lies between the left ventricle (LV) and the aorta. More particularly, a valve prosthesis 100 is shown in its compressed or delivery configuration in the side views of FIG. 1A and FIG. 1B and in its expanded or deployed configuration in the side views of FIG. 2A and FIG. 2B. Valve prosthesis 100 includes a framework or stent 102, a valve component 116 attached within the interior portion of stent or frame 102, and one or more elements 120 for positioning and/or sealing. As will be explained in more detail herein, each element 120 bends or rotates more than ninety degrees with respect to its compressed, delivery configuration during deployment of valve prosthesis 100. In one embodiment, each element 120 rotates between 135 degrees and 180 degrees during deployment of valve prosthesis 100. In the delivery configuration of FIG. 1A and FIG. 1B, each element 120 distally extends from a distal end 104 of stent 102. When released from a delivery sheath (not shown in FIG. 1A or FIG. 1B), each element 120 gradually bends outwardly and then towards an outer surface of the delivery device or stent until it reaches its deployed configuration of FIG. 2A and FIG. 2B in which each element 120 proximally extends from distal end 104 of stent 102. Once deployed, elements 120 may function to position and anchor valve prosthesis 100 at a native valve target site and/or elements 120 may function to seal prosthesis 100 at a native valve target site. When deployed at a native mitral valve target site, the configuration/structure of a valve prosthesis as well as the delivery system and method of use must accommodate the size of the left ventricle and refrain from obstructing the left ventricular outflow tract. By rotating from an initial distally-extending configuration to a final proximally-extending configuration, elements 120 may be particularly configured to be deployed within a native mitral valve target site as will be explained in more detail below.

Stent 102 of valve prosthesis 100 is a generally tubular expandable body having a stepped profile extending between a proximal end 106 and distal end 104. As shown in the deployed configuration of FIG. 2A and FIG. 2B, stent 102 may include a distal or ventricular segment 108 having an expanded diameter $D_V$ and a proximal or atrial segment 110 having an expanded diameter $D_A$ which is greater than diameter $D_V$. In one embodiment, when placed at a native mitral valve target site, ventricular segment 108 extends into the left ventricle and atrial segment 110 extends into the left atrium. Each segment of stent 102, i.e., ventricular segment 108 and/or atrial segment 110, may be designed with a number of different configurations and sizes to meet the different requirements of the locations in which it may be implanted. Each segment of stent 102, i.e., ventricular segment 108 and/or atrial segment 110, may have the same or different cross-section which may be for example circular, ellipsoidal, rectangular, hexagonal, square, or other polygonal shape, although at present it is believed that circular or ellipsoidal may be preferable when the valve prosthesis is being provided for replacement of the mitral valve.

In embodiments hereof, stent 102 may be made from stainless steel, a pseudo-elastic metal such as a nickel titanium alloy or Nitinol, or a so-called super alloy, which may have a base metal of nickel, cobalt, chromium, or other metal. Stent 102 is self-expanding to return to an expanded deployed state from a compressed or constricted delivery state. "Self-expanding" as used herein means that stent 102 has a mechanical memory to return to the expanded or deployed configuration. Mechanical memory may be imparted to the wire or tubular structure that forms stent 102 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. For self-expanding stent structures, one example of a delivery system that can be used includes a catheter with a retractable sheath that covers and compresses the stent and its associated valve structure until it is to be deployed, at which point the sheath can be retracted to allow the stent frame to assume its expanded or deployed configuration. Further details of such a delivery process for delivering stented valve prostheses as described herein are discussed in further detail below.

Figure 5:
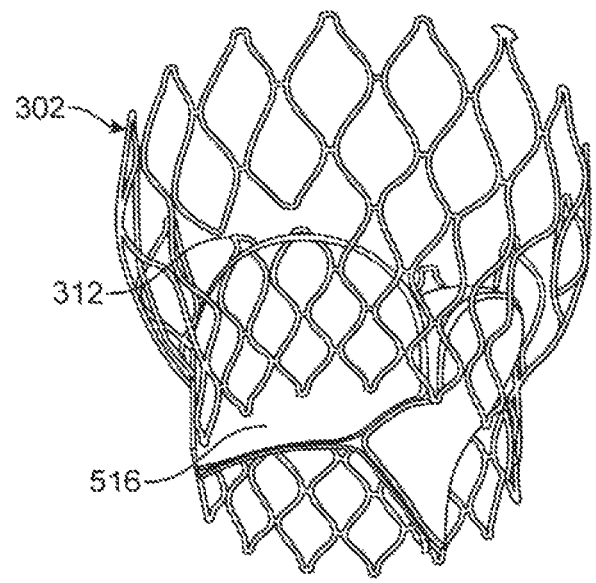
FIG. 5 is an isometric view illustration of the exemplary stent of FIG. 3, wherein the stent is in an expanded or deployed configuration and includes a prosthetic valve located therein.
Figure 6:
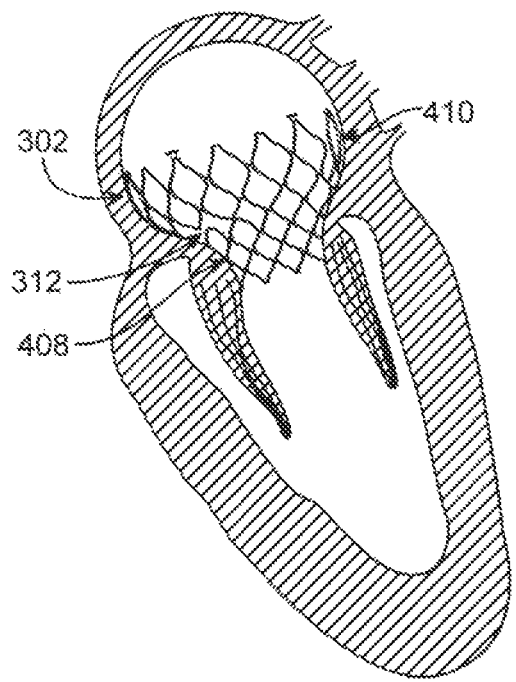
FIG. 6 is a side view illustration of the exemplary stent of FIG. 3, wherein the stent is in an expanded or deployed configuration and positioned within at a mitral valve of a heart.

As shown in FIGS. 3-6, stent 302 has a lattice configuration 314, with connectors 303 extending from an end of stent 302 for connecting to a delivery system (not shown). Stent 302 is shown in a compressed configuration and deployed configuration in FIG. 3 and FIG. 4, respectively. Similar to stent 102, stent 302 includes an expandable body having a stepped outer diameter formed by a distal or ventricular segment 408 having an expanded diameter $D_V$ and a proximal or atrial segment 410 having an expanded diameter $D_A$ which is greater than diameter $D_V$. Stent 302 is shown deployed at a native mitral valve target site in FIG. 6, with ventricular segment 408 extending into the left ventricle and atrial segment 410 extending into the left atrium. Stent 302 is a unitary integral structure formed from a single tubular component. Lattice configuration 314 of stent 302 may be produced by machining or laser cutting the stent from a metal tube, as is commonly employed in the manufacturing of stents. Lattice configuration 314 includes disconnected or decoupled turns or crowns 312 at the transition area between ventricular segment 408 and atrial segment 410, which advantageously allows leaflets of a valve component 516 to extend into atrial segment 410 (and into the left atrium when in situ) as shown in FIG. 5 rather than be solely located on the outflow or ventricular segment 408 of stent 302 (and into the left ventricle in situ). By locating a portion of the valve leaflets in the left atrium, the required length of ventricular segment 408 is minimized and the length of the stent that protrudes into the left ventricle may be reduced. Further description of stent 302 and advantages thereof are described in co-pending patent application, U.S. application Ser. No. 13/278,050 filed Oct. 20, 2011. Although stent 302 is shown with a lattice configuration, it will be understood by those of ordinary skill in the art that the body of stent 302 may have any configuration or pattern suitable for placement at a native mitral valve target site.

As mentioned above, a stent of valve prosthesis 300 may be laser cut from a solid component of self-expanding material such that the stent is an integral structure that does not include individual components. A single integral structure allows the stent to be crimped or compressed to a low delivery profile. Alternatively, rather than being laser cut, the stent may be formed using any of a number of different methods that would be apparent to one of ordinary skill in the art such as connecting individual annular stent struts together, chemical etching, or another method of cutting a desired shape from a solid component.

Referring back to FIGS. 1A, 1B, 2A, and 2B, valve prosthesis 100 includes prosthetic valve component 116 within the interior of stent 102 which is capable of blocking flow in one direction to regulate flow there through. Prosthetic valve component 116 may include valve leaflets constructed of pericardium material and may form a bicuspid, tricuspid, or tubular replacement valve. FIG. 1A, FIG. 1B, FIG. 2A, and FIG. 2B illustrate an exemplary bicuspid valve having two leaflets 118A, 118B, although a tricuspid leaflet configuration may alternatively be used in embodiments hereof.

Valve leaflets 118 are sutured or otherwise securely and sealingly attached to the interior surface of stent 102 and/or graft material (not shown) enclosing or lining one or more portions of stent 102 as would be known to one of ordinary skill in the art of prosthetic tissue valve construction. The graft material may be a low-porosity woven fabric, such as polyester, Dacron fabric, or PTFE, which creates a one-way fluid passage when attached to the stent. In one embodiment, the graft material may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the graft material could also be a natural material such as pericardium or another membranous tissue such as intestinal submucosa.

As described above, leaflets 118 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 118 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Elements 120 for positioning and/or sealing will now be described in more detail. Referring also to FIG. 26A, elements 120 are generally shown in the figures as being a wire or tubular structure formed into a U-shaped or generally U-shaped configuration such that each element 120 has two straight side segments 2680A, 2682A with a bottom curved segment 2684A. As will be understood by those of ordinary skill in the art, "side" and "bottom" are relative terms and utilized herein for illustration purposes only. The straight side segments may be parallel to each other as shown in FIG. 26A, or may be slanted or angled away from each other as shown in FIG. 26B in which two straight slanted side segments 2680B, 2682B flare apart as they extend from bottom curved segment 2684B. As utilized herein, "generally" U-shaped includes wire or tubular structures formed into: a horseshoe shape as shown in FIG. 26C in which two curved side segments 2680C, 2682C have ends that converge together as they extend from bottom curved segment 2684C; a semi-circle 2620D as shown in FIG. 26D; and an oblong shape 2620F as shown in FIG. 26F in which two parallel straight side segments 2680F, 2682F have a straight bottom segment 2684F therebetween. In another embodiment hereof, elements 120 may be generally V-shaped as shown in FIG. 26E in which two straight slanted side segments 2680C, 2682C are connected together by a curved apex 2684E. The elements 120 may be considerably longer, shorter, wider, or narrower than shown. In any case, elements 120 are preferably configured to be a shape and size that can provide a sealing function, a positioning function and/or an anchoring function for valve prosthesis 100 when the prosthesis is deployed at a native valve target site. For example, if valve prosthesis 100 is positioned within the native mitral valve annulus, the elements 120 extend from stent 102 on the ventricular or outflow side of the mitral valve and provide interference with the native valve leaflets and/or the walls of the left ventricle, thereby inhibiting motion of valve prosthesis 100.

Figure 7A:
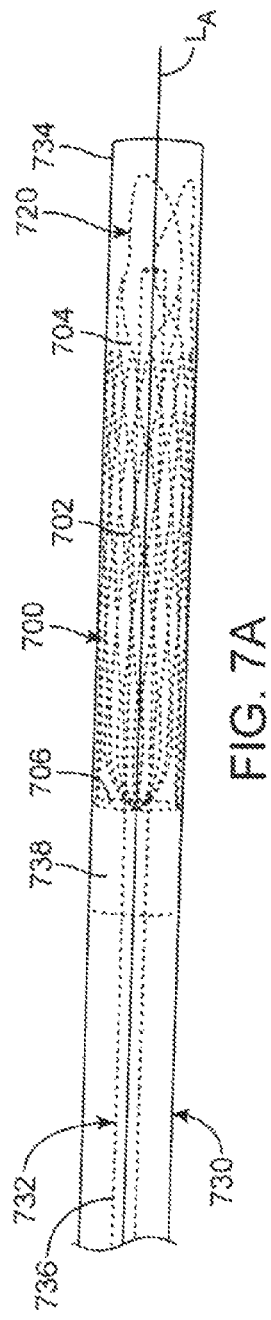
FIGS. 7A and 7B illustrate side and end views, respectively, of a valve prosthesis in an unexpanded or delivery or compressed configuration, loaded into a delivery system, according to an embodiment hereof.
Figure 7B:
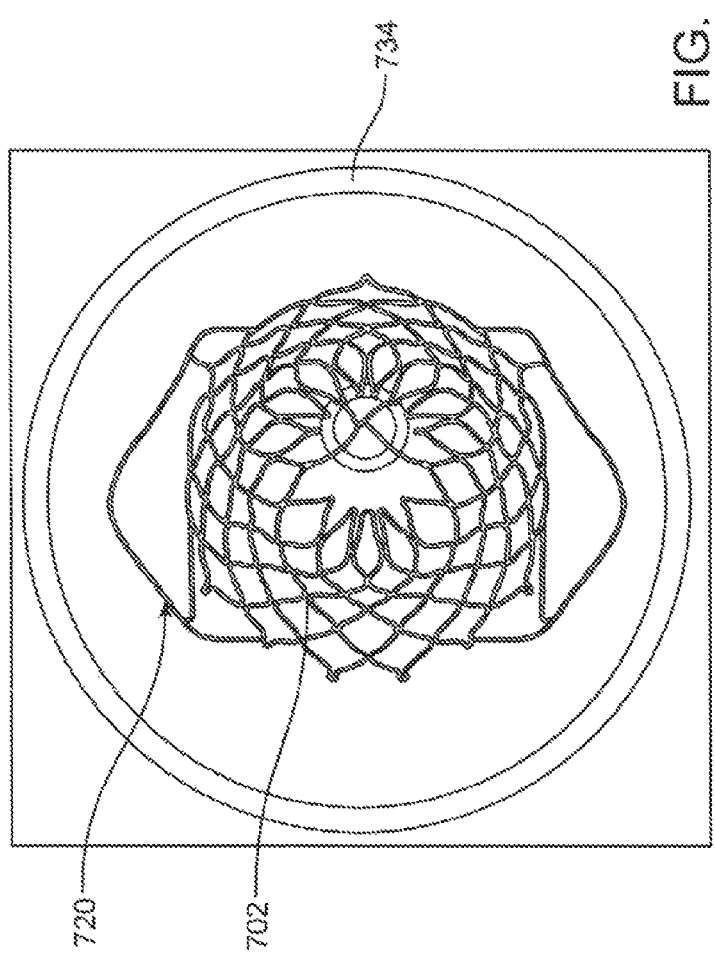

Each element 120 rotates and transforms from the distally-extending compressed configuration to proximally-extending deployed configuration. FIG. 7A and FIG. 7B illustrate side and end views, respectively, of a valve prosthesis 700 in an compressed or delivery configuration sized for delivery to the target site, loaded into a delivery system 730. Valve prosthesis 700 includes a tubular frame or stent 702 which is similar to stent 302 described above, a valve (not shown in FIGS. 7-13 for illustrative purposes) attached within the interior portion of stent 702, and two elements 720. In the compressed or delivery configuration, each element 720 is approximately parallel with a longitudinal axis $L_a$ of stent 702 and distally extends from a distal end 704 of stent 702. Delivery system 730 includes a catheter 732 and an outer retractable sheath or tube 734. Valve prosthesis 700 is mounted over an inner shaft 736 of catheter 732 at the distal end thereof and sheath 734 surrounds and constrains valve prosthesis 700 in the compressed configuration. In one embodiment, catheter 732 may also include a retainer 738 which temporarily secures proximal end 706 of stent 702 onto catheter 732. For example, retainer 738 may include an end stent capture con-figuration as described in U.S. Patent Pub. 2009/0276027 to Glynn, which is hereby incorporated by reference herein in its entirety.

Figure 8:
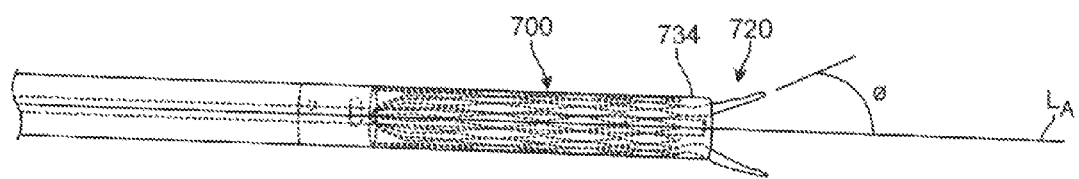
FIGS. 8-10 illustrate side views of the valve prosthesis of FIG. 7, wherein a sheath of the delivery system is progressively retracted to expose the positioning and/or sealing elements of the valve prosthesis.

In order to begin deployment of valve prosthesis 700, sheath 734 is retracted in a proximal direction to expose and release elements 720 as shown in FIG. 8. Upon initial release from sheath 734, elements 720 flare or spread outwardly from the distal end of stent 702 such that elements 720 form an acute angle Ø with respect to longitudinal axis $L_a$.

Figure 9:
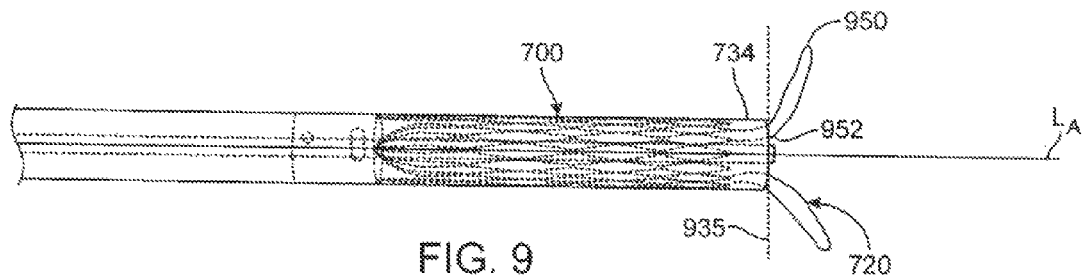
Figure 10:
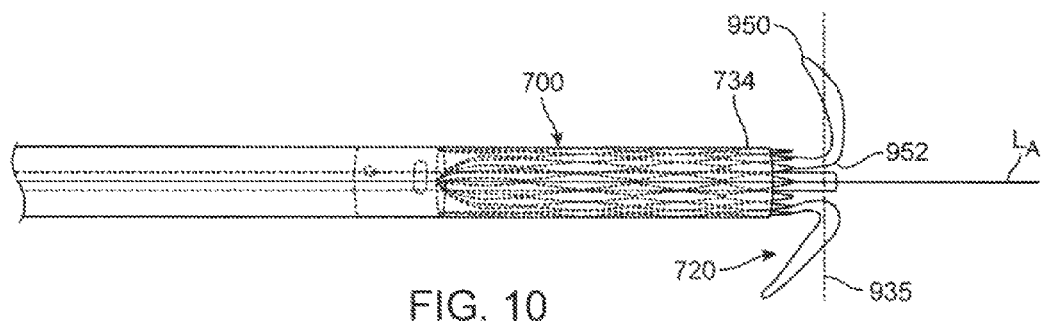

As sheath 734 is further retracted, elements 720 continue to be exposed and continue to bend backwards towards the outer surface of sheath 734 and stent 702. Notably, as elements 720 are released from sheath 734, stent 702 remains constrained within sheath 734. FIG. 9 illustrates elements 720 approaching a transverse reference axis 935 between the initial distally-extending compressed configuration and the final proximally-extending deployed configuration. Transverse reference axis 935 as utilized herein describes an imaginary reference line that extends approximately ninety degrees or perpendicular to the longitudinal axis La of stent 702. FIG. 10 illustrates elements 720 after passing over the transverse reference axis 935, with elements 720 fully exposed or released from sheath 734 while stent 702 is still compressed within sheath 734. One particular feature of elements 720 is apparent when comparing FIG. 9 and FIG. 10. Elements 720 bend or curve gradually backwards such that distal portions or tips 950 of elements 720 pass over the transverse reference axis 935 before proximal portions or bases 952 of elements 720. After distal tips 950 of elements 720 pass or cross over the transverse reference axis 935 and are pointing in a proximal direction, proximal bases 952 of elements 720 approach the transverse reference axis 935 as shown in FIG. 10. Stated another way, distal tips 950 of each element 720 bend past transverse reference axis 935 prior to proximal bases 952 of each element 720. Due to the above-described flaring or expanding sequence in which elements 720 curve backward, the length of elements 720 may be greater than if both the proximal and distal portions of elements 720 crossed over the transverse reference axis 935 at the same time, i.e., if elements 720 were straight and extended generally parallel to the transverse reference axis 935 during deployment. In addition, since stent 702 is still compressed within sheath 734, it can be observed that the length of elements 720 may be greater than if stent 702 was released from sheath 734 and in a deployed configuration. Accordingly, the length of elements 720 may be maximized to increase their ability to anchor valve prosthesis 700 when it is positioned to replace a valve. In one embodiment in which valve prosthesis 700 is positioned at a mitral valve, the length of each element 720 is between 10 and 12 mm.

Figure 13:
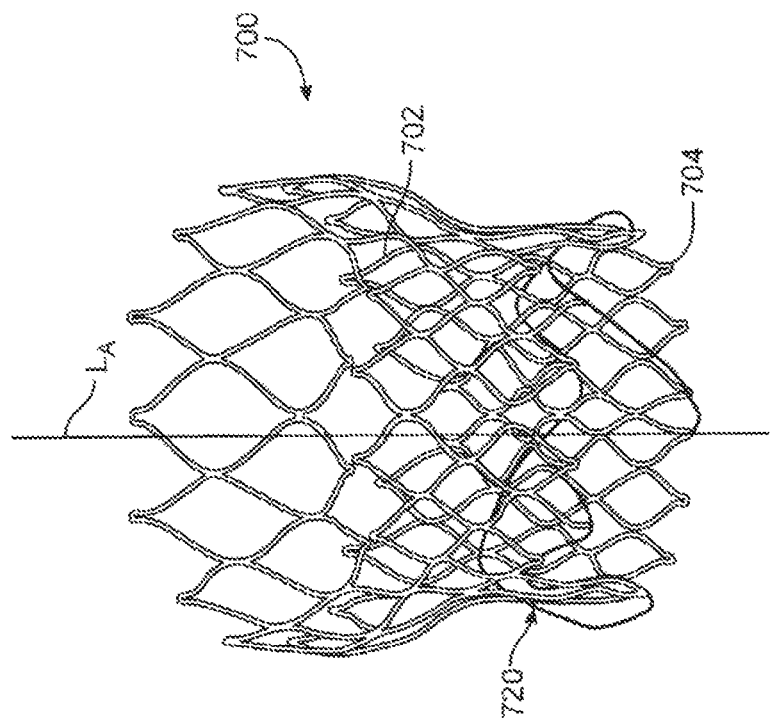
FIG. 13 illustrates a side view of the valve prosthesis of FIG. 7 in an expanded or deployed configuration, after release from the delivery system.
Figure 11:
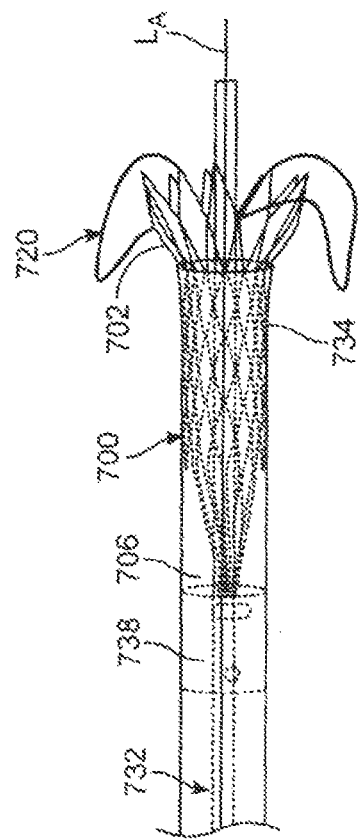
FIGS. 11-12 illustrate side views of the valve prosthesis of FIG. 7, wherein a sheath of the delivery system is progressively retracted to expose the stent of the valve prosthesis.
Figure 12:
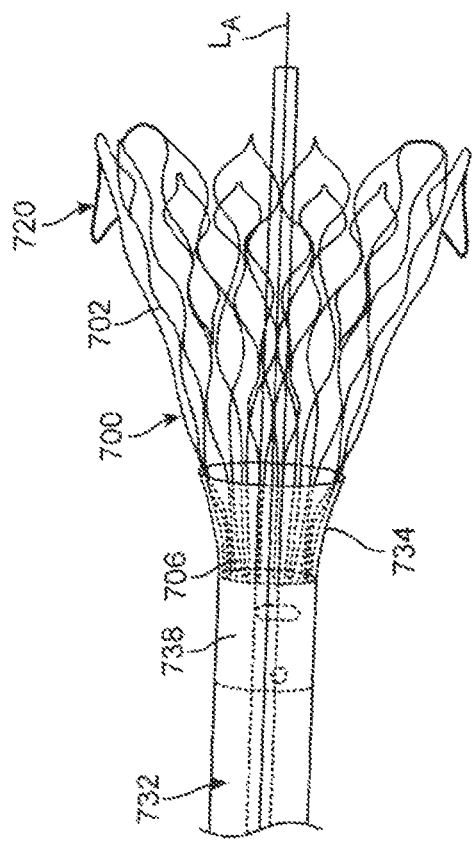

FIG. 11 and FIG. 12 illustrate the continued deployment of valve prosthesis 700. Sheath 734 continues to be proximally retracted, exposing self-expanding stent 702 such that stent 702 is released to assume its deployed configuration. Sheath 734 is proximally retracted until proximal end 706 of stent 702 is exposed and allowed to self-expand, thereby uncoupling from retaining tip 738 of catheter 732. FIG. 13 illustrates the final deployed configuration of valve prosthesis 700, in which each element 720 proximally extends from a distal end 704 of stent 702. As previously described, the backwards rotation that occurs during deployment results in each element 720 translating more than ninety degrees from its compressed, delivery configuration. During deployment, each element 720 essentially deploys or translates in an arc path that extends between 90 and 180 degrees from the initial compressed configuration and the final deployed configuration. In the embodiment of FIG. 13 shown ex vivo, each element 720 bent or rotated approximately 180 degrees between the initial distally-extending compressed configuration and the final proximally-extending deployed configuration. However, in one embodiment, when positioned in vivo, tissue such as native valve leaflets may be sandwiched between one or more elements 720 and the outer surface of stent 702 and as a result, the total rotation or bending of elements 720 in the final deployed configuration may be less than 180 degrees with respect to the initial distally-extending compressed configuration.

In one embodiment, rotating from the initial distally-extending configuration to the final proximally-extending configuration allows valve prosthesis 700 to be deployed in the annulus of a native mitral valve rather than the outflow side of the native mitral valve, thereby minimizing the length which the prosthesis and the delivery system protrudes into the left ventricle. More particularly, prior art approaches for delivering a valve prosthesis include initially loading positioning or anchoring elements into the delivery system as proximally-extending, such that the positioning elements are pressed against the stent of the valve prosthesis. Such initially proximally-extending positioning elements flare outward or away from the stent less than ninety degrees when released from a delivery sheath to a final deployed configuration. In order to properly position positioning elements that initially extend in a proximal direction at a mitral valve location, the valve prosthesis would need to be distally extended past the native mitral valve and into the left ventricle prior to retraction of the delivery sheath in order to provide ample space for the positioning elements to deploy. After the positioning elements flared to the acutely angled deployed configuration, the prosthesis would be proximally retracted in order to bring the positioning elements into contact with the native mitral valve. However, in embodiments hereof, since positioning elements are initially loaded into delivery system 730 as distally-extending, valve prosthesis 700 is initially positioned in the annulus of the native mitral valve with only distally-extending positioning elements 720 extending into the left ventricle prior to retraction of the delivery sheath.

In addition, the fact that elements 720 are deployable via one delivery sheath helps accommodate deployment of valve prosthesis 700 at a native mitral valve despite constraints or considerations of delivering a prosthesis in a left ventricle. In some aortic valve applications, multiple tubes are utilized for deploying stented cardiac valve prosthetics. For example, the ENGAGER device from Medtronic, Inc. of Minneapolis, Minn. is a stented cardiac valve prosthesis having positioning elements in which two tubes are utilized for deployment. A first distal cone or tube is distally advanced into the aorta during deployment to deploy the positioning elements and then a second proximal sleeve is proximally retracted to deploy stent frame. However, when deploying a valve prosthesis at a mitral valve target location, distally advancing a tube or sheath into the left ventricle may damage chordae tendineae located within the heart and/or may obstruct the left ventricular outflow tract (LVOT). In addition, the mitral valve is positioned lower in the heart than the aortic valve and thus there is not as much depth/length to distally advance a tube or sheath into the left ventricle. Accordingly, valve prosthesis 700 is deployed via delivery system 730 that includes only one delivery sheath 734 which is proximally retracted.

In order to transform between the initial distally-extending compressed configuration and the final proximally-extending deployed configuration, elements for positioning and/or sealing according to embodiments described herein are formed from a self-expanding material that has a mechanical memory to return to the proximally-extending deployed configuration. For example, the elements for positioning and/or sealing may be made from stainless steel, a pseudo-elastic metal such as a nickel titanium alloy or Nitinol, or a so-called super alloy, which may have a base metal of nickel, cobalt, chromium, or other metal. As described above with respect to stent 102, mechanical memory may be imparted to the wire or tubular structure that forms the elements for positioning and/or sealing by thermal treatment to achieve a spring temper in stainless steel, for example, or to set a shape memory in a susceptible metal alloy, such as nitinol, or a polymer.

In one embodiment, as previously described, each element for positioning and/or sealing is coupled to the distal end of the valve prosthesis. In one embodiment, each element for positioning and/or sealing may be coupled to the stent at multiple connection points. More specifically referring to FIG. 1A, U-shaped support arm 122A is coupled to distal end 104 of stent 102 via two V-shaped connectors 124A, 125A such that four connection points 126A, 127A, 128A, 129A are located between each element 120 and stent 102. Similarly, shown in the view of FIG. 14, U-shaped support arm 122B is coupled to distal end 104 of stent 102 via two V-shaped connectors 1248, 1258 such that four connection points 126B, 127B, 128B, 129B are located between each element 120 and stent 102. In one embodiment, the eight connection points 126A, 127A, 128A, 129A, 126B, 127B, 128B, 129B are approximately equally spaced around the perimeter of distal end 104 of stent 102 and collectively function to prevent the prosthetic valve leaflets from obstructing the outflow end of valve prosthesis 100 and the left ventricular outflow tract (LVOT). Stated another way, V-shaped connectors 124A, 125A, 124B, 1258 increase the number of connection points between each support arm 120A, 1208, respectively, and stent 102, and thereby shorten or minimize the open space or distance between adjacent connection points. V-shaped connectors 124A, 125A, 124B, 1258 act as an obstacle in the path that the prosthetic valve leaflets would follow when overlapping onto stent 102 and thereby keeps the flow path clear. Although described as "V-shaped connectors," it will be apparent to those of ordinary skill in the art that two straight components formed generally in the shape of a "V" may be utilized in embodiments hereof rather than one single V-shaped component. In addition, although described with respect to elements 120 and stent 102, such connectors may be utilized for forming multiple connection points between any embodiment described herein, including elements 320 and stent 302, and elements 720 and stent 702.

In one embodiment, elements 120 and stent 102 are formed as an integral unitary structure, such as by laser cutting or etching elements 120 and stent 102 from a single hollow tube or sheet. In another embodiment, V-shaped connectors 124A, 124B and/or U-shaped support arms 122A, 122B, may be separate components that are formed separately and mechanically coupled to each other and to stent 102 via any suitable mechanical method, including welding, soldering, or by another mechanical method.

Figure 15:
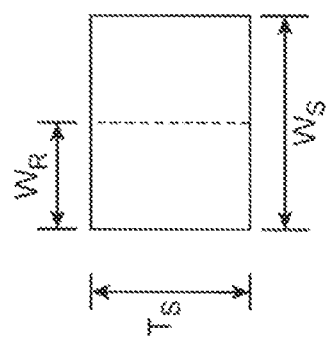
FIG. 15 is a cross-sectional view taken along line X-X of FIG. 14.
Figure 14:
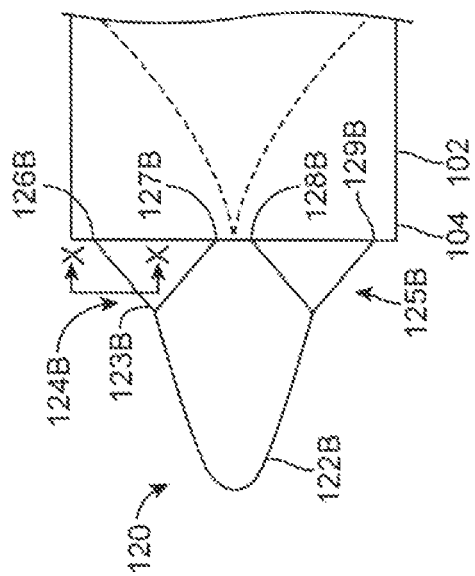
FIG. 14 is a side-view illustration of a portion of the valve prosthesis of FIG. 1, wherein each element for positioning and/or sealing is coupled to the stent at four connection points.

In order to lower the amount of stress and/or strain that occurs in V-shaped connectors 124A, 125A, 124B, 125B as elements 120 transform, for example, between the initial distally-extending compressed configuration and the final proximally-extending deployed configuration, the width of the wire(s) or tubular member(s) which form V-shaped connectors 124A, 125A, 124B, 125B may be increased as compared to the width or dimension of U-shaped support arms 122A, 122B as well as compared to the width or dimension of the wire or tubular member which forms stent 102. More particularly, FIG. 15 illustrates a sectional view along line X-X of FIG. 14 showing a strut 123B of V-shaped connector 124B according to one embodiment hereof. A reference width $W_R$ is shown in phantom in FIG. 15 and represents the width of the wire or tubular member which forms stent 102 and/or U-shaped support arms 122A, 122B. A width $W_S$ of strut 123B is widened or increased relative to width $W_R$, thereby increasing the amount of material of V-shaped connector 1248 such that it can handle the deformation that occurs thereto during deployment of valve prosthesis 100. In order to widen or increase the width of strut 1238, material may be added or banded to strut 1238 around the width direction thereof. In an embodiment, material may be added to include the width of strut 123B up to three times of width $W_R$. Preferably, a thickness $T_S$ of strut 123B is not increased relative to the thickness of the wire or tubular member which forms stent 102 due to size constraints on the compressed outer diameter or profile of valve prosthesis 100 when in the compressed configuration. As utilized herein, thickness $T_S$ of strut 123B refers to the strut material that extends in a radial direction relative to stent 102. Although illustrated as constant or uniform, thickness $T_S$ of strut 123B may vary or increase from an inner surface relative to an outer surface of strut 123B.

Figure 16:
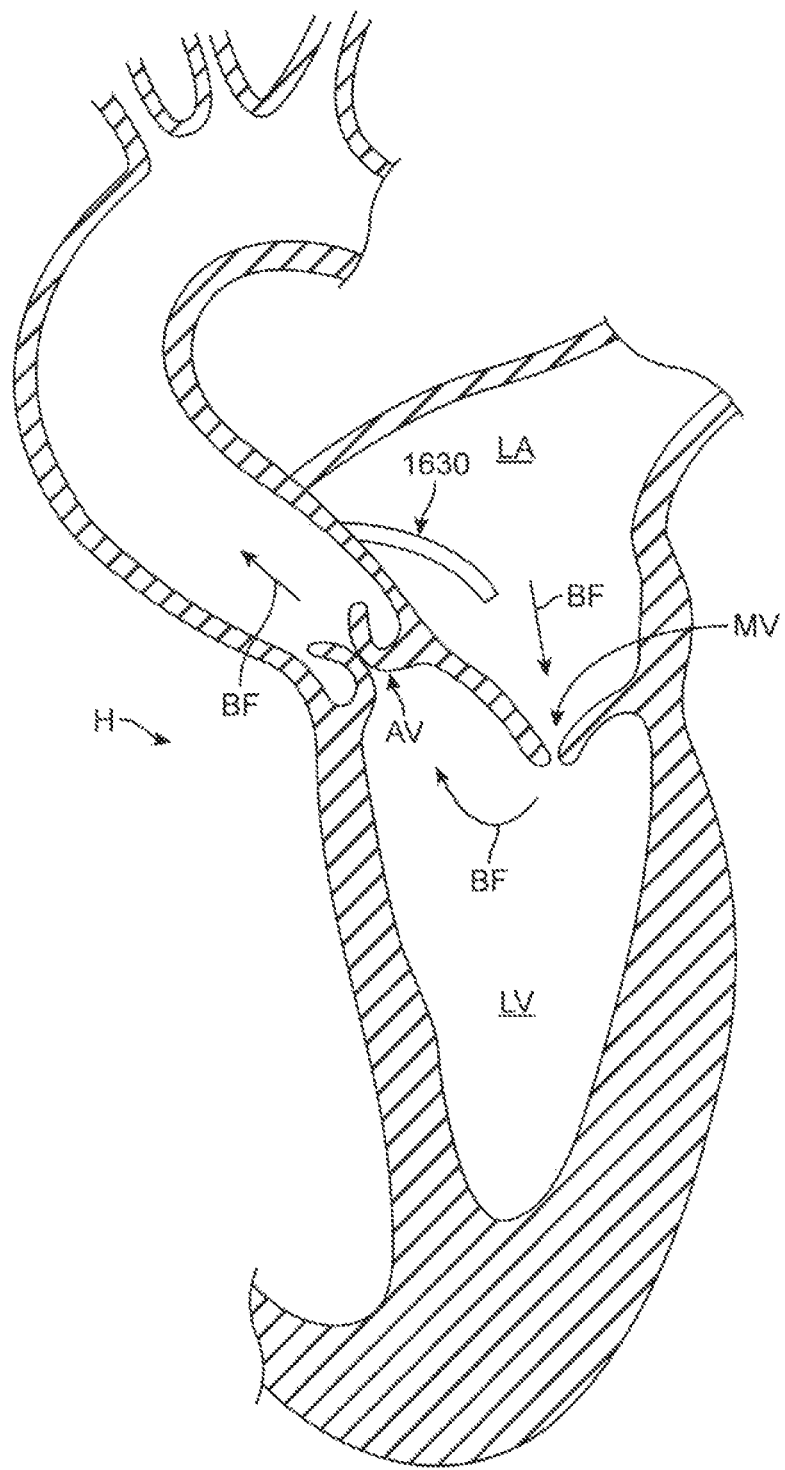
FIG. 16 through FIG. 20 illustrates a method of implanting a valve prosthesis at a mitral valve target location within a heart, according to an embodiment hereof.

FIGS. 16-20 illustrate a method of delivering and implanting stent valve prosthesis 100 in accordance with an embodiment hereof to perform a heart valve replacement procedure, more particularly a mitral valve replacement, with minimal blood flow stoppage or interruption. FIG. 16 illustrates a portion of a heart H including a left atrium LA, a left ventricle LV, a mitral valve space MV and an aortic valve AV. Blood flow BF is depicted with directional arrows in FIG. 16 in the left atrium LA, into left ventricle LV through mitral valve space MV, and into the aorta through aortic valve AV. When the native mitral valve is operating properly, the native leaflets will generally function in such a way that blood flows toward the left ventricle LV when the leaflets are in an open position, and so that blood is prevented from moving toward the left atrium LA when the leaflets are in a closed position. However, a valve prosthesis in accordance with an embodiment hereof can be positioned in the area of mitral valve MV when it is not functioning properly (to replace the mitral valve) in accordance with the invention, thereby pushing the native leaflets out of the mitral valve space.

With reference to FIG. 16, a prosthetic valve delivery system 1630 is shown after having been introduced into the vasculature via a percutaneous entry point, a.k.a the Seldinger technique, and having been tracked through the vasculature and into the left atrium so that distal tip 1640 is positioned proximate the mitral valve. For example, the percutaneous entry point may be formed in a femoral vein. Thereafter, a guidewire (not shown) is advanced through the circulatory system, eventually arriving at the heart. The guidewire is directed into the right atrium, traverses the right atrium and is made to puncture with the aid of a transeptal needle or pre-existing hole, the atrial septum, thereby entering the left atrium. Once the guidewire is positioned, the endoluminal entry port and the atrial septum are dilated to permit entry of a guide catheter (not shown) and/or prosthetic valve delivery system 1630 into the left atrium. Thereafter, prosthetic valve delivery system 1630 is advanced into the left atrium through the punctured atrial septum and positioned proximate to the mitral valve MV. Although not shown, it will be understood by those of ordinary skill in the art that prosthetic valve delivery system 1630 may be inserted into a guide catheter in order to be advanced to a position proximate to the mitral valve MV. In addition, although described as a transfemoral antegrade approach for percutaneously accessing the mitral valve, the valve prosthesis 100 may be positioned within the desired area of the heart via entry other different methods such as a transseptal antegrade approach via a thoracotomy for accessing the mitral valve.

Figure 17:
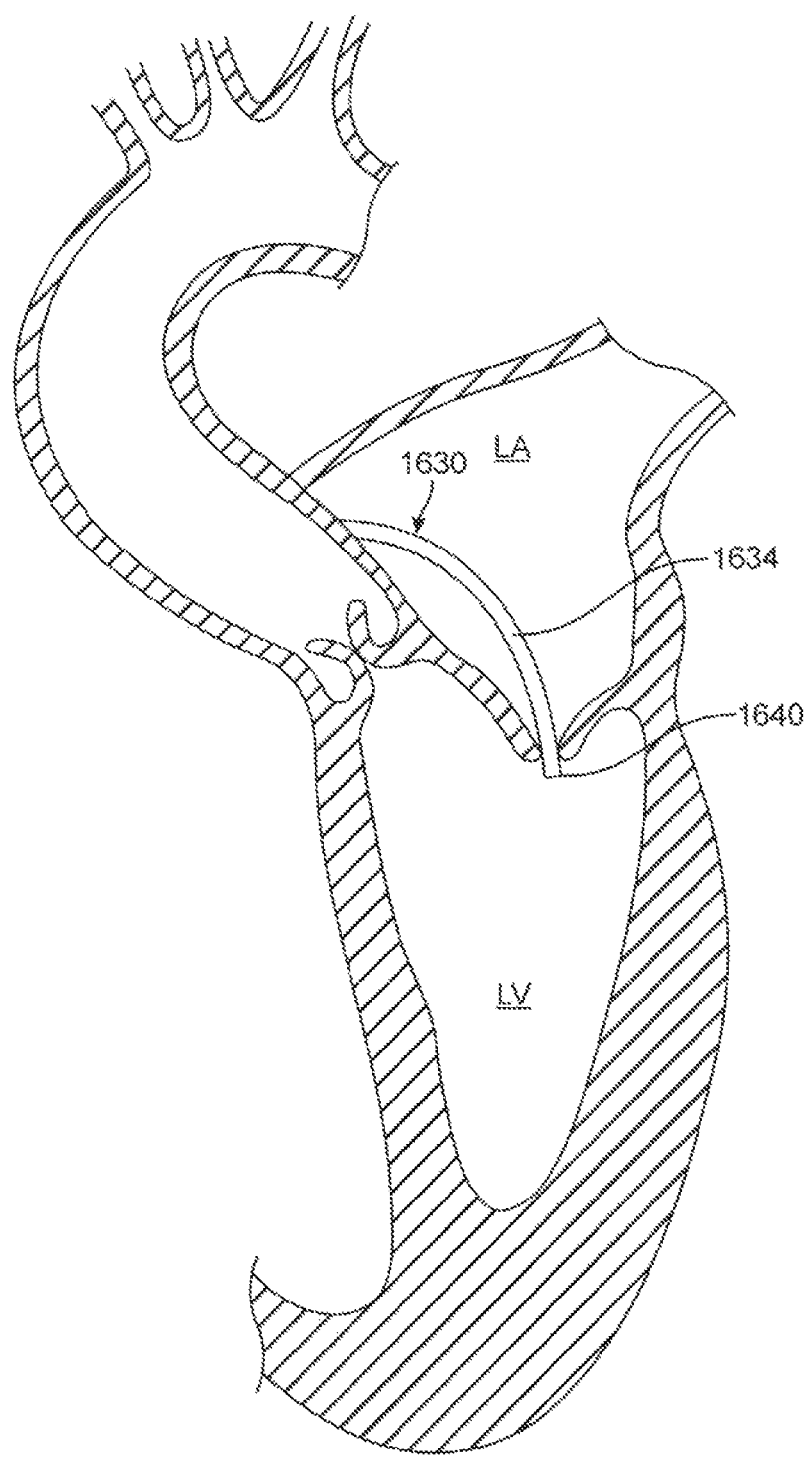

Similar to delivery system 730 described above with respect to FIGS. 7A, 7B and 8-13, prosthetic valve delivery system 1630 includes an outer retractable sheath or tube 1634 positioned over the a catheter (not shown in FIGS. 16-20) having compressed valve prosthesis 100 to keep it from expanding and to minimize interference between the valve prosthesis and the vasculature through which it will be traveling. Valve prosthesis 100 is mounted over an inner shaft of the catheter at the distal end thereof and sheath 1634 surrounds and constrains valve prosthesis 100 in the compressed configuration. After being advanced into the left atrium LA, prosthetic valve delivery system 1630 including sheath 1634 may then be advanced through the mitral valve MV and into the left ventricle LV as shown in FIG. 17. Distal tip 1640 of prosthetic valve delivery system 1630 is advanced into the left ventricle LV until valve prosthesis 100 is centered at the native mitral valve, i.e., deployed in the annulus of the native mitral valve, with elements 120 of valve prosthesis 100 contained within sheath 1634 and distally extending into the left ventricle LV. As previously discussed, deploying valve prosthesis 100 in the middle of the native valve rather than the outflow side of the native mitral valve minimizes the length which the prosthesis and the delivery system protrudes into the left ventricle.

Figure 18:
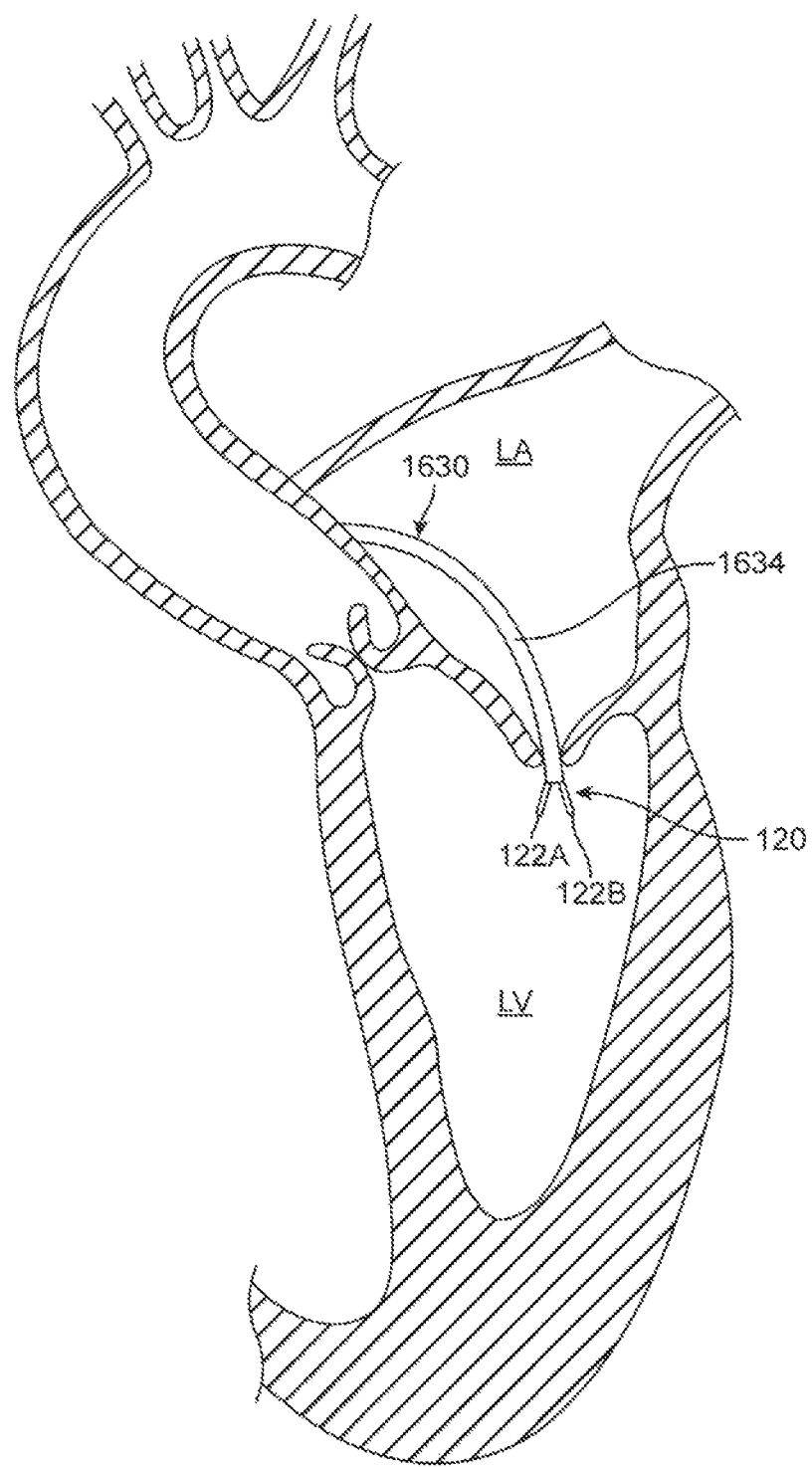

Referring now to FIG. 18, when valve prosthesis 100 is in position in the middle of the native mitral valve, elements 120 of valve prosthesis 100 are released by retracting sheath 1634 of prosthetic valve delivery system 1630 by a sufficient amount that this portion of the prosthesis is exposed. Due to the self-expanding properties of the elements 120, support arms 122A, 122B will expand radially outwardly relative to the sheath in which it was enclosed. As shown FIG. 18, and also referring to FIG. 8 described above, upon initial release from sheath 1634, elements 120 flare or spread outwardly from the outer surface of the remainder of the prosthesis such that elements 120 are acutely angled with respect to longitudinal axis $L_a$. During the transformation between the distally-extending compressed configuration and the proximally-extending deployed configuration, support arms 122A, 122B are located on outflow side, i.e., the left ventricle LV side, of the mitral valve while stent 102 of prosthesis 100 is positioned within the mitral valve and still contained within sheath 1634.

Figure 19:
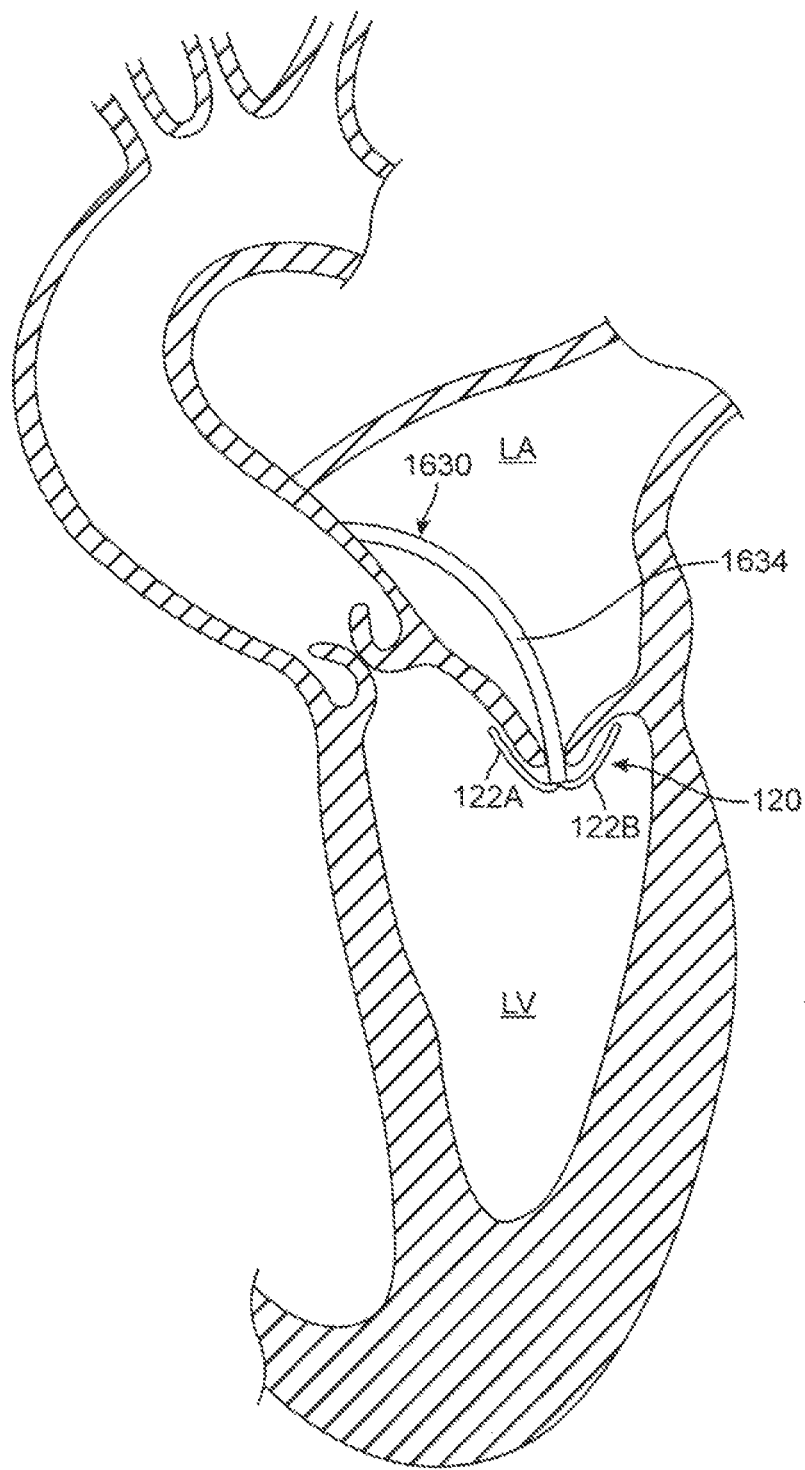

Exposure and rotation of elements 120 continues as sheath 1634 is retracted. FIG. 19 illustrates elements 120 fully exposed or released from sheath 1634 while stent 102 is still compressed within sheath 1634. Elements 120 are now proximally extending, and support arms 122A, 122B firmly press against the native mitral valve leaflets and/or the left ventricle LV in order to position valve prosthesis 100.

Figure 20:
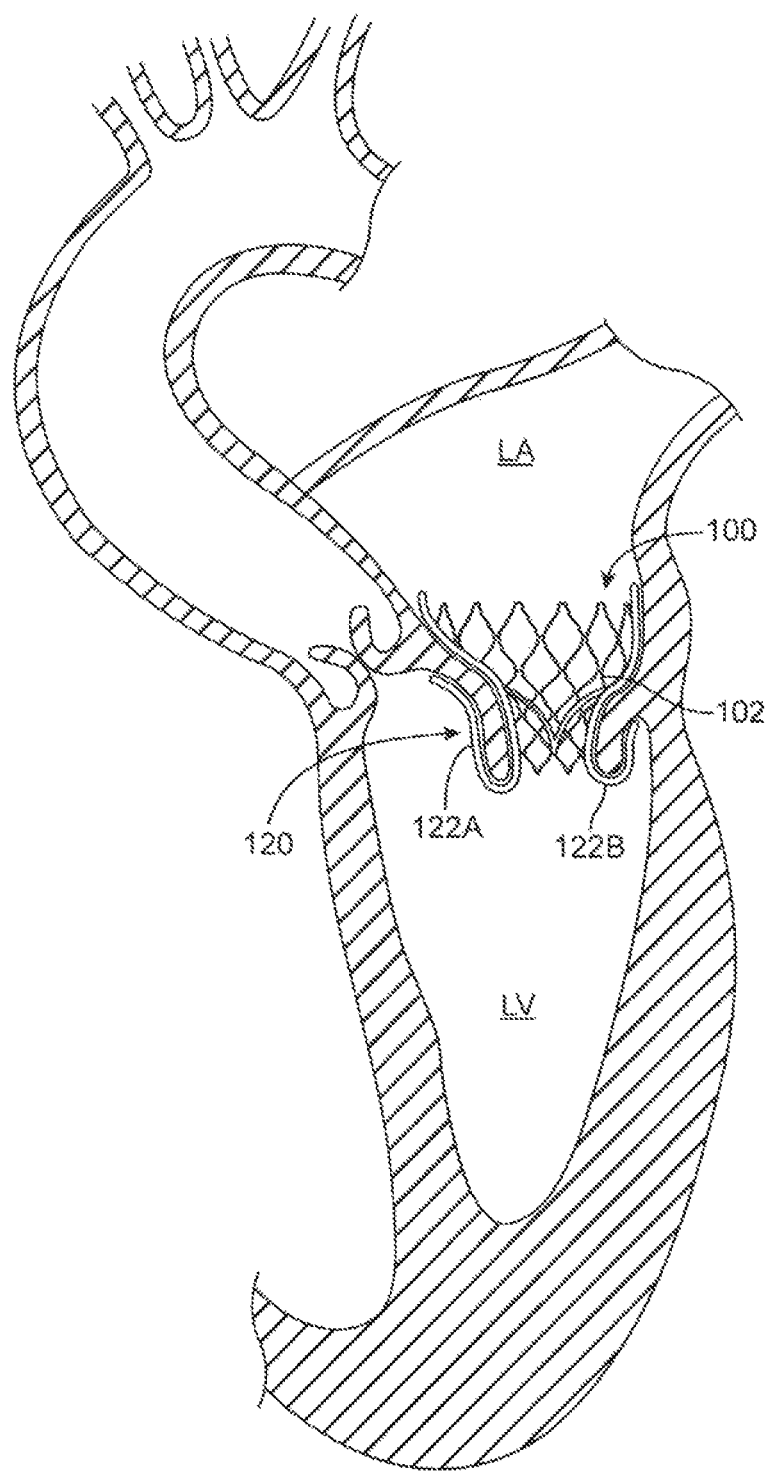
Figure 22A:
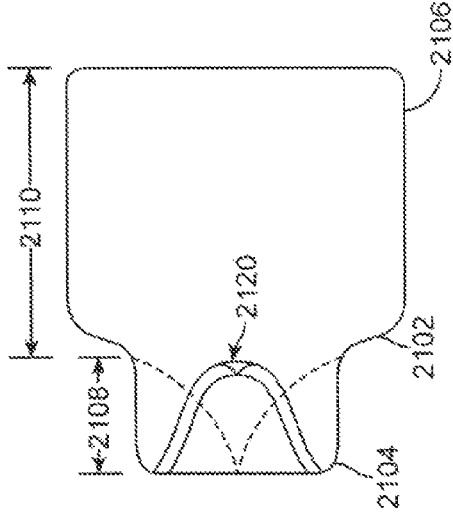
FIG. 22A and FIG. 22B are schematic side and top views, respectively, of the valve prosthesis of FIG. 21A and FIG. 21B, wherein the valve prosthesis is in an expanded or deployed configuration with elements for positioning and/or sealing proximally extending from a distal end of the prosthesis.
Figure 22B:
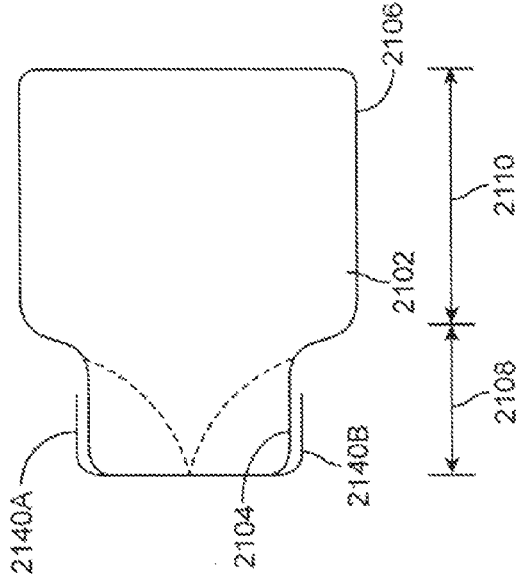
Figure 21A:
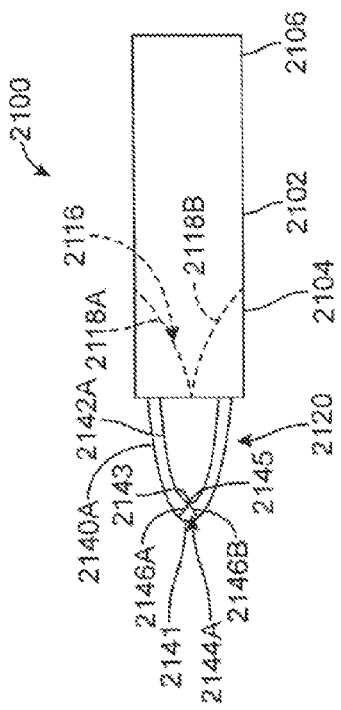
FIG. 21A and FIG. 21B are schematic side and top views, respectively, of a valve prosthesis having elements for positioning and/or sealing with outer and inner U-shaped support arms according to an embodiment hereof, wherein the valve prosthesis is in a delivery or compressed configuration with elements for positioning and/or sealing distally extending from a distal end of the prosthesis.
Figure 21B:
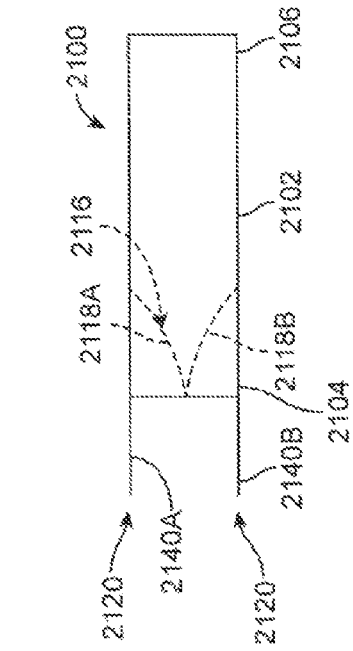

After elements 120 are deployed to anchor or hold valve prosthesis 100 in place as desired, sheath 1634 continues to be proximally retracted, exposing self-expanding stent 102 such that stent 102 is released from the delivery system to assume its deployed configuration. Due to the self-expanding properties of the stent frame, stent 102 will expand outwardly relative to the sheath in which it was enclosed. Sheath 1634 is proximally retracted until the proximal end of stent 102 is exposed and allowed to self-expand, thereby uncoupling the prosthesis from catheter 1632. The delivery system can then be retracted from the patient, leaving the expanded prosthesis 100 deployed at the mitral valve as shown in FIG. 20. In the final deployed configuration of valve prosthesis 100, each element 120 proximally extends from a distal end 104 of stent 102. Each element 120 rotates in a radial direction between 90 and 180 degrees from the initial distally-extending compressed configuration to the final proximally-extending deployed configuration until support arms 122A, 122B firmly press against the native mitral valve leaflets and/or the left ventricle LV in order to position valve prosthesis 100. The amount or degree of rotation may depend upon a patient's individual anatomy and state of the native mitral valve leaflets.

FIGS. 21A, 21B, 22A, 22B illustrates another embodiment of elements for positioning and/or sealing with double or dual support arms that may be utilized in any embodiment described herein. More particularly, a valve prosthesis 2100 is shown in its compressed or delivery configuration in the side views of FIG. 21A and FIG. 21B and in its expanded or deployed configuration in the side views of FIG. 22A and FIG. 22B. Similar to embodiments described above, valve prosthesis 2100 includes a framework or stent 2102, a valve component 2116 attached within the interior portion of stent 2102 that is capable of blocking flow in one direction to regulate flow through valve prosthesis 2100 via leaflets 2118A, 2118B, and elements 2120 for positioning and/or sealing. Stent 2102 of valve prosthesis 2100 is a generally tubular expandable body having a stepped outer diameter or profile extending between a proximal end 2106 and distal end 2104. Similar to embodiments described above, the stepped outer diameter of stent 2102 includes a distal or ventricular segment 2108 and a proximal or atrial segment 2110 having an expanded diameter which is greater than the expanded diameter of distal segment 2108.

In one embodiment, elements 2120 for positioning and/or sealing extend from opposing sides of stent 2102. Each element 2120 may include a first or outer U-shaped support arm 2140A, 2140B, respectfully, and a second or inner U-shaped support arm 2142A that each distally extend from a distal end 2104 of stent 2102. The second or inner U-shaped support arm adjacent to outer U-shaped support arm 2140B is obscured from view in the figures, but it will be understood by those of ordinary skill in the art that each element 2120 may include both an outer U-shaped support arm and an inner U-shaped support arm. When released from a delivery sheath (not shown), each of the U-shaped support arms gradually bends outwardly and then towards an outer surface of the delivery device or stent until they transform from their compressed configuration of FIG. 21A and FIG. 21B to their deployed configuration of FIG. 22A and FIG. 22B in which each of the U-shaped support arms proximally extends from distal end 2104 of stent 2102. As in embodiments described above, each of the U-shaped support arms bends or rotates more than ninety degrees with respect to its compressed, delivery configuration during deployment of valve prosthesis 2100. In one embodiment, each U-shaped support arm rotates between 135 degrees and 180 degrees during deployment of valve prosthesis 2100. Compared to a single U-shaped support arm, outer and inner U-shaped support arms provide each element 2120 with additional spring force for improved sealing, anchoring and/or positioning of the valve prosthesis.

Adjacent outer and inner U-shaped support arms of each element for positioning and/or sealing are coupled together via a connector 2144A which ensures that both U-shaped support arms of the element for positioning and/or sealing remain in the same plane during deployment. Connector 2144A has a flared V-shaped configuration in which an apex 2145 of connector 2144A is coupled to a peak or crest 2143 of inner support arm 2142A. More particularly, connector 2144A includes two curved legs 2146A, 2146B. First ends of legs 2146A, 2146B are coupled to peak 2143 of inner support arm 2142A, and curved legs 2146A, 2146B of connector 2144A extend or flare away from each other such that second ends of legs 2146A, 2146B are coupled adjacent to or on opposing sides of a peak or crest 2141 of outer support arm 2140A. Due to the curved legs 2146A, 2146B of connector 2144A, the distance or space between the crowns of outer and inner U-shaped support arms is adjustable and allowed to change. Legs 2146A, 2146B allow the distance or space between peak 2143 of inner support arm 2142A and peak 2141 of outer support arm 2140A because the curved legs of connector 2144A may bend, resulting in a shorter distance between peak 2143 and peak 2141, or the legs of connector 2144A may straighten, resulting in a greater distance between peak 2143 and peak 2141. The distance or space between peak 2143 and peak 2141 may increase during crimping when valve prosthesis 2100 is in its compressed configuration shown in FIG. 21A, 21B, and the distance or space may decrease during expansion when valve prosthesis 2100 is in its deployed configuration. Connector 2144A, as well as the inner and outer U-shaped support arms, may be laser cut from a tube of self-expanding material and thereby integrally formed as part of the stent, or may be formed separately and subsequently attached to the stent. Although connector 2144A is only visible in FIGS. 21A, 21B, 22A, 22B between inner support arm 2142A and outer support arm 2140A, it will be understood by those of ordinary skill in the art that such a connector couples the outer and inner support arms of each element for positioning and/or sealing extending from the prosthesis.

FIGS. 23A, 23B, 23C illustrate an embodiment of a valve prosthesis 2300 including a lattice framework or stent 2302 and elements 2320 for positioning and/or sealing with dual U-shaped support arms that distally extend from a distal end 2304 of the valve prosthesis. More particularly, elements 2320 include a first or outer U-shaped support arm 2340A, 2340B, respectfully, and a second or inner U-shaped support arm 2342A, 2342B that each bend or rotate more than ninety degrees with respect to its compressed, delivery configuration during deployment. Each outer support arm is connected to its respective inner support arm via a connector 2344A, as described above with respect to connector 2144A. In the embodiment of FIGS. 23A, 23B, 23C, the U-shaped support arms extend from the distalmost crowns or apexes 2353 of lattice stent 2302. Compared to the embodiment shown in FIGS. 24A-24C, stent 2302 has a smaller crimped profile for delivery.

Figure 24A:
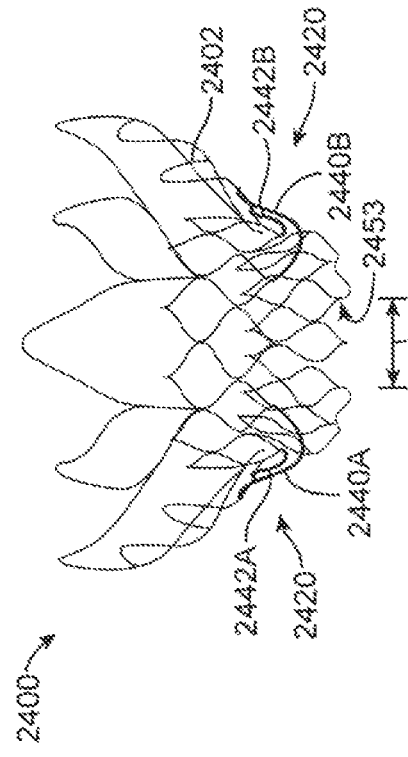
FIGS. 24A and 24B illustrate two side views of a valve prosthesis having elements for positioning and/or sealing with outer and inner U-shaped support arms according to an embodiment hereof, wherein the support arms extend from between the distalmost crowns of the valve prosthesis and the valve prosthesis is in an expanded or deployed configuration.
Figure 24B:
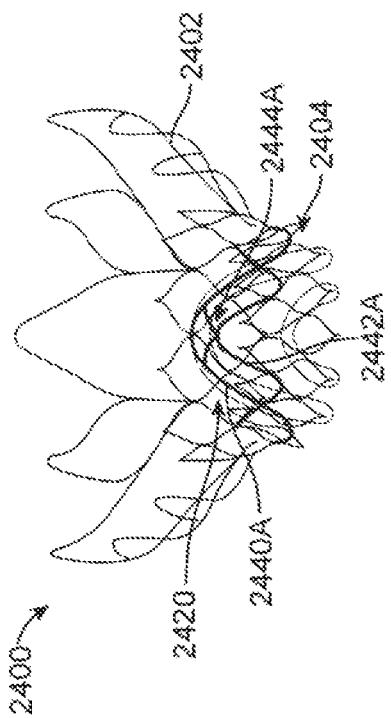
Figure 24C:
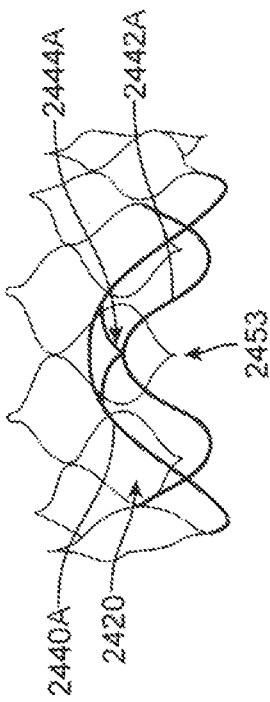
FIG. 24C is an enlarged view of a portion of the valve prosthesis of FIG. 24A.

FIGS. 24A, 24B, 24C illustrate an embodiment of a valve prosthesis 2400 that is similar to valve prosthesis 2300, except that elements 2420 for positioning and/or sealing do not extend from distalmost crowns or apexes 2453 of a lattice stent 2402. Rather, elements 2420 extend from between the distalmost crowns or apexes 2453 of lattice stent 2402. As best shown in FIG. 24B, in order to shorten or minimize the open space or distance 2450 between adjacent elements 2420, elements 2420 extend from opposing sides of a distalmost crown 2453 such that elements 2420 are separated only by the width of the crown. More particularly, elements 2420 distally extend from a distal end 2404 of the valve prosthesis and include a first or outer U-shaped support arm 2440A, 2440B, respectfully, and a second or inner U-shaped support arm 2442A, 2442B that each bend or rotate more than ninety degrees with respect to its compressed, delivery configuration during deployment. Each outer support arm is connected to its respective inner support arm via a connector 2444A, as described above with respect to connector 2144A. Elements 2420 extend from between the distalmost crowns or apexes 2453 of lattice stent 2402 to minimize open space or distance 2450 and thereby prevent the prosthetic valve leaflets from obstructing the outflow end of valve prosthesis 2400 and the left ventricular outflow tract (LVOT). Outer U-shaped support arms of elements 2420 are closer together, and act as an obstacle in the path that the prosthetic valve leaflets would follow when overlapping onto stent 2402 and thereby keeps the flow path clear. Another benefit of extending elements 2420 from between the distalmost crowns or apexes 2453 of lattice stent 2402 is that elements 2420 are located more proximal along the prosthesis compared to the embodiment shown in FIGS. 23A-23C, which minimizes the length or amount of material that projects or extends in the left ventricle.

Figure 25B:
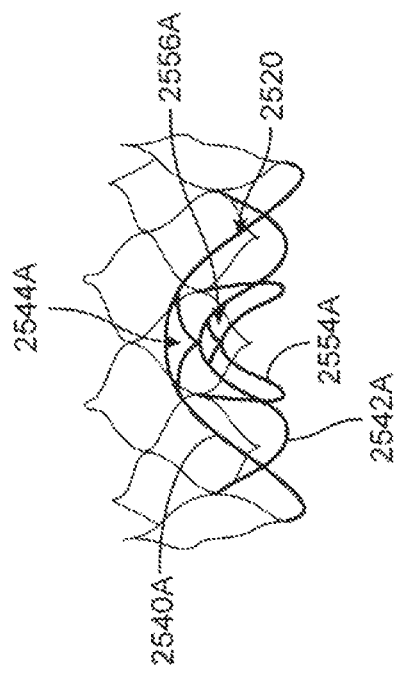
FIG. 25B is an enlarged view of a portion of the valve prosthesis of FIG. 25A.
Figure 25A:
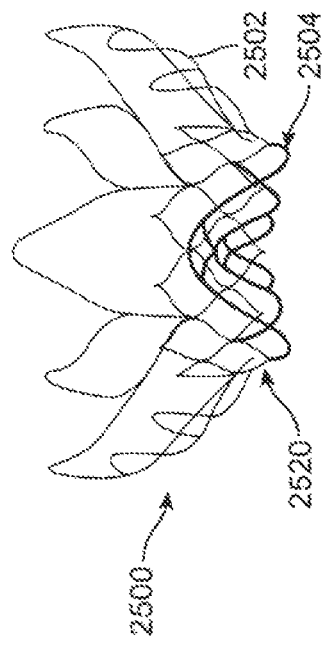
FIG. 25A is a side view of a valve prosthesis having elements for positioning and/or sealing with triple U-shaped support arms according to an embodiment hereof, wherein the valve prosthesis is in an expanded or deployed configuration.

FIGS. 25A and 25B illustrate another embodiment of a valve prosthesis 2500 that is similar to valve prosthesis 2400, except that each element 2520 for positioning and/or sealing includes triple support arms for additional spring force for improved sealing, anchoring and/or positioning of the valve prosthesis. Each element 2520 extends from between the distalmost crowns of a distal end 2504 of a lattice stent 2502 and includes a first or outer U-shaped support arm 2540A, a second or intermediate U-shaped support arm 2542A, and a third or inner U-shaped support arm 2554A. When released from a delivery sheath (not shown in FIG. 25A or FIG. 25B), all of the U-shaped support arms gradually bend outwardly and then towards an outer surface of the delivery device or stent until they reach their deployed configuration of FIG. 25A and FIG. 25B in which all of the U-shaped support arms proximally extend from distal end 2504 of stent 2502. As in embodiments described above, all of the U-shaped support arms bend or rotate more than ninety degrees with respect to its compressed, delivery configuration during deployment of valve prosthesis 2500. In one embodiment, each U-shaped support arm rotates between 135 degrees and 180 degrees during deployment of valve prosthesis 2100. Although only one element 2520 is shown in described in FIGS. 25A, 25B, it will be understood by those of ordinary skill in the art that valve prosthesis 2500 may include at least two elements for positioning and/or sealing extending from opposing sides of the prosthesis. Each element 2520 may include triple U-shaped support arms for sealing, anchoring and/or positioning the valve prosthesis.

Adjacent U-shaped support arms of each element 2520 are coupled together via a connector which ensures that each support arm of element 2520 remains in the same plane during deployment. More specifically, outer U-shaped support arm 2540A is coupled to intermediate U-shaped support arm 2542A via a connector 2544A and intermediate U-shaped support arm 2542A is coupled to inner U-shaped support arm 2554A via a connector 2556A. Connectors 2544A, 2556A have the same flared V-shaped configuration as connector 2144A described above. Due to the curved or flared legs of connectors 2544A, 2556A, the distance or space between the peaks of adjacent U-shaped support arms is adjustable and allowed to change as described with respect to connector 2144A.

Figure 27:
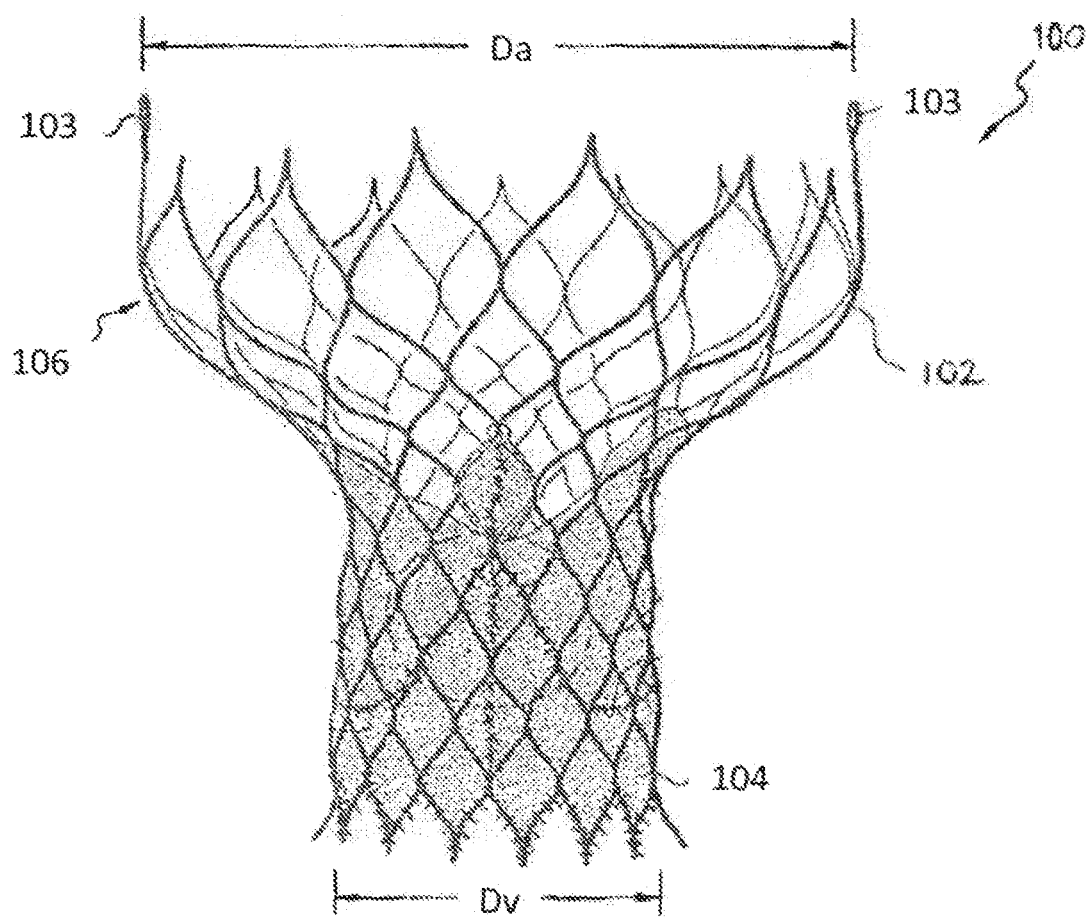
FIG. 27 is a side view illustration of an exemplary valve prosthesis.

FIG. 27 depicts an exemplary transcatheter heart valve prosthesis 100. Heart valve prosthesis 100 is illustrated herein in order to facilitate description of the methods and devices to prevent and/or repair paravalvular leakage according to embodiments hereof. It is understood that any number of alternate heart valve prostheses can be used with the methods and devices described herein. Heart valve prosthesis 100 is merely exemplary and is described in more detail in U.S. Patent Application Pub. No. 2011/0172765 to Nguyen et al., which is herein incorporated by reference in its entirety.

Heart valve prosthesis 100 may include an expandable stent or frame 102 that supports a prosthetic valve component within the interior of stent 102. In some embodiments, stent 102 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration. Mechanical memory may be imparted to the wire or tubular structure that forms stent 102 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. Alternatively, heart valve prosthesis 100 may be balloon-expandable as would be understood by one of ordinary skill in the art.

In one embodiment, stent 102 of valve prosthesis 100 has a deployed configuration including a proximal end 106 and a distal end 104. As shown in the deployed configuration of FIG. 27, distal end 104 may have an expanded diameter $D_V$ and proximal end 106 may have an expanded diameter $D_A$ which is greater than diameter $D_V$. In one embodiment, when placed at a native aortic valve target site, distal end 104 extends into the left ventricle and proximal end 104 extends into the aorta. Each portion of stent 102, i.e., distal end portion 104 and/or proximal end portion 106, may be designed with a number of different configurations and sizes to meet the different requirements of the locations in which it may be implanted. Each portion or segment of stent 102, for example, distal end portion 104 and/or proximal end portion 106, may have the same or different cross-section which may be for example circular, ellipsoidal, rectangular, hexagonal, square, or other polygonal shape, although at present it is believed that circular or ellipsoidal may be preferable when the valve prosthesis is being provided for replacement of the mitral valve. When configured as a replacement for an aortic valve, distal end 104 functions as an inflow end of heart valve prosthesis 100 and extends into and anchors within the aortic annulus of a patient's left ventricle, while proximal end 106 functions as an outflow end of heart valve prosthesis 100 and is positioned in the patient's ascending aorta. When configured as a replacement for a mitral valve, proximal end 106 functions as an inflow end of heart valve prosthesis 100 and is positioned in the patient's left atrium, while distal end 104 functions as an outflow end of heart valve prosthesis 100 and extends into and anchors within the mitral annulus of a patient's left ventricle. For example, U.S. Patent Application Publication Nos. 2012/0101572 to Kovalsky et al. and 2012/0035722 to Tuval, each of which are herein incorporated by reference in their entirety, illustrate heart valve prostheses configured for placement in a mitral valve. In various embodiments, valve prosthesis 100 when deployed may have an hourglass configuration, a generally tubular configuration, or other stent configurations or shapes known in the art for valve replacement. Stent 102 also may include eyelets or connectors 103 that may extend from either end or both ends thereof for use in loading the heart valve prosthesis 100 into a delivery catheter.

As previously mentioned, heart valve prosthesis 100 includes a prosthetic valve component 116 within the interior of stent 102. The prosthetic valve component is capable of blocking flow in one direction to regulate flow there through via valve leaflets 118 that may, for example, form a bicuspid or tricuspid replacement valve. More particularly, if heart valve prosthesis 100 is configured for placement within a native valve having three leaflets such as the aortic, tricuspid, or pulmonary valves, heart valve prosthesis 100 may include three valve leaflets 118. If heart valve prosthesis 100 is configured for placement within a native valve having two leaflets such as the mitral valve, heart valve prosthesis 100 may include two valve leaflets 118. Valve leaflets 118 may be sutured or otherwise securely and sealingly attached to the interior surface of stent 102 and/or graft material which may enclose or line stent 102 as would be known to one of ordinary skill in the art of prosthetic tissue valve construction. Adjoining pairs of leaflets may be attached to one another at their lateral ends to form commissures, with free edges of the leaflets forming coaptation edges that meet in area of coaptation.

Leaflets 118 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 118 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets may be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material may also be a natural or biological material such as pericardium or another membranous tissue such as intestinal submucosa. Alternatively, graft material may be a low-porosity woven fabric, such as polyester, Dacron fabric, or PTFE, which creates a one-way fluid passage when attached to the stent. In one embodiment, graft material may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

In one embodiment, delivery of heart valve prosthesis 100 may be accomplished via a percutaneous transfemoral approach. During delivery, the prosthetic valve remains compressed until it reaches a target diseased native heart valve, at which time the heart valve prosthesis 100 can be released from the delivery catheter and expanded in situ via self-expansion. The delivery catheter is then removed and heart valve prosthesis 100 remains deployed within the native target heart valve.

Figure 28:
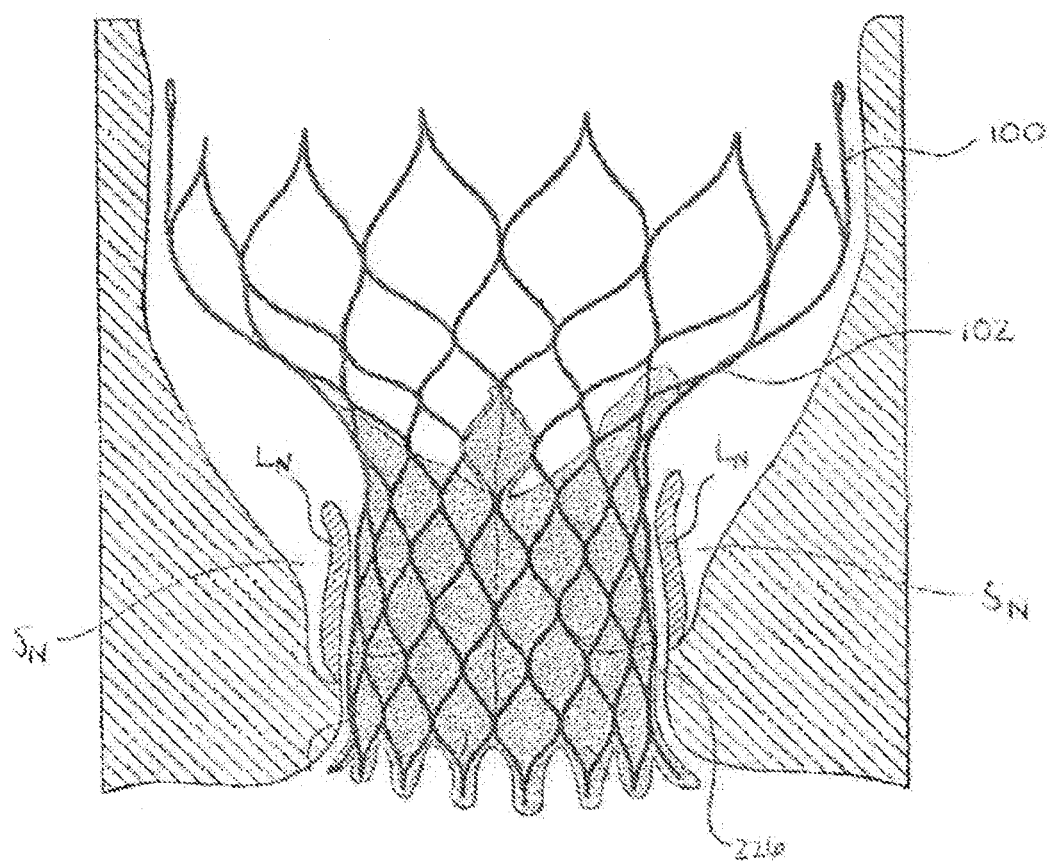
FIG. 28 is a side view illustration of the valve prosthesis of FIG. 27 implanted within a native valve annulus.

FIG. 28 is a side view illustration of heart valve prosthesis 100 implanted within a native heart valve, which is shown in section, having native leaflets $L_N$ and corresponding native sinuses $S_N$. In one embodiment, when heart valve prosthesis 100 is deployed within the valve annulus of a native heart valve, stent 102 expands within native valve leaflets $L_N$ of the patient's defective valve, retaining the native valve leaflets in a permanently open state. The native valve annulus may include surface irregularities on the inner surface thereof, and as a result one or more gaps or crevices 226 may be present or may form between the perimeter of heart valve prosthesis 100 and the native valve annulus. For example, calcium deposits may be present on the native valve leaflets (e.g., stenotic valve leaflets) and/or shape differences may be present between the native heart valve annulus and prosthesis 100. More particularly, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site.

Figure 29:
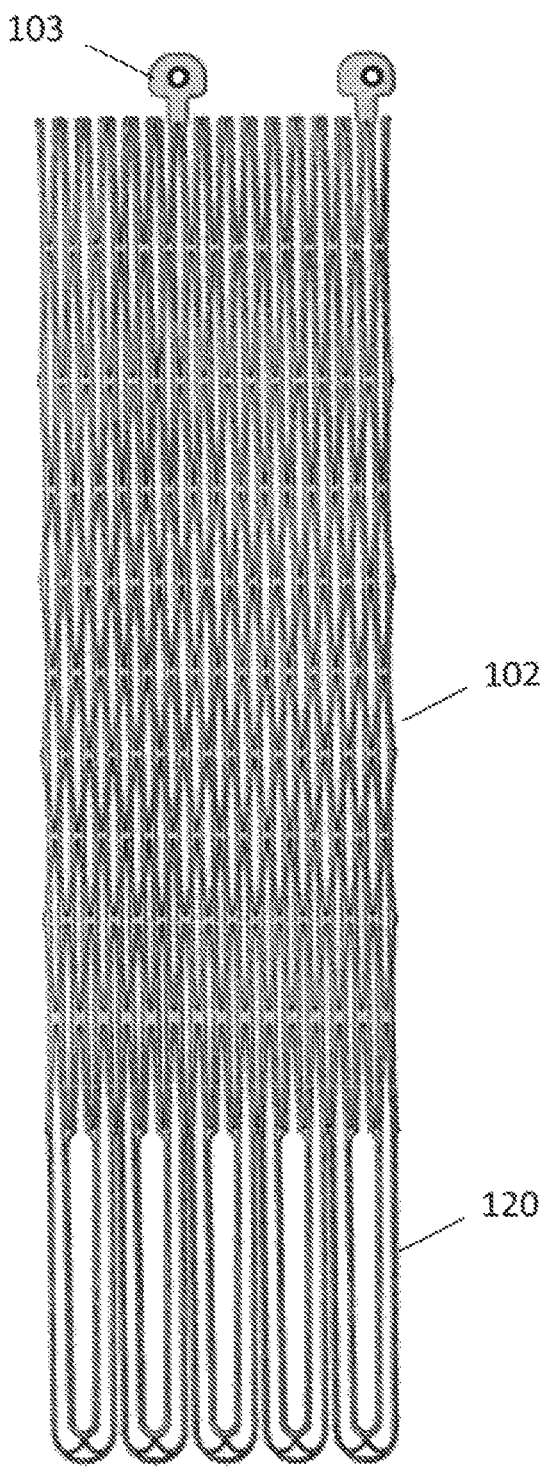
FIG. 29 is a side view illustration of a stent that may be utilized in a valve prosthesis for use in embodiments hereof, wherein the stent is in a delivery or compressed configuration.

In one embodiment, as shown in FIG. 29, stent 102 has a lattice configuration, which is shown in a compressed configuration. Stent 102 may be a unitary integral structure formed from a single tubular component. Stent 102 may be produced by machining or laser cutting the stent from a metal tube, as is commonly employed in the manufacturing of stents.

Figure 30:
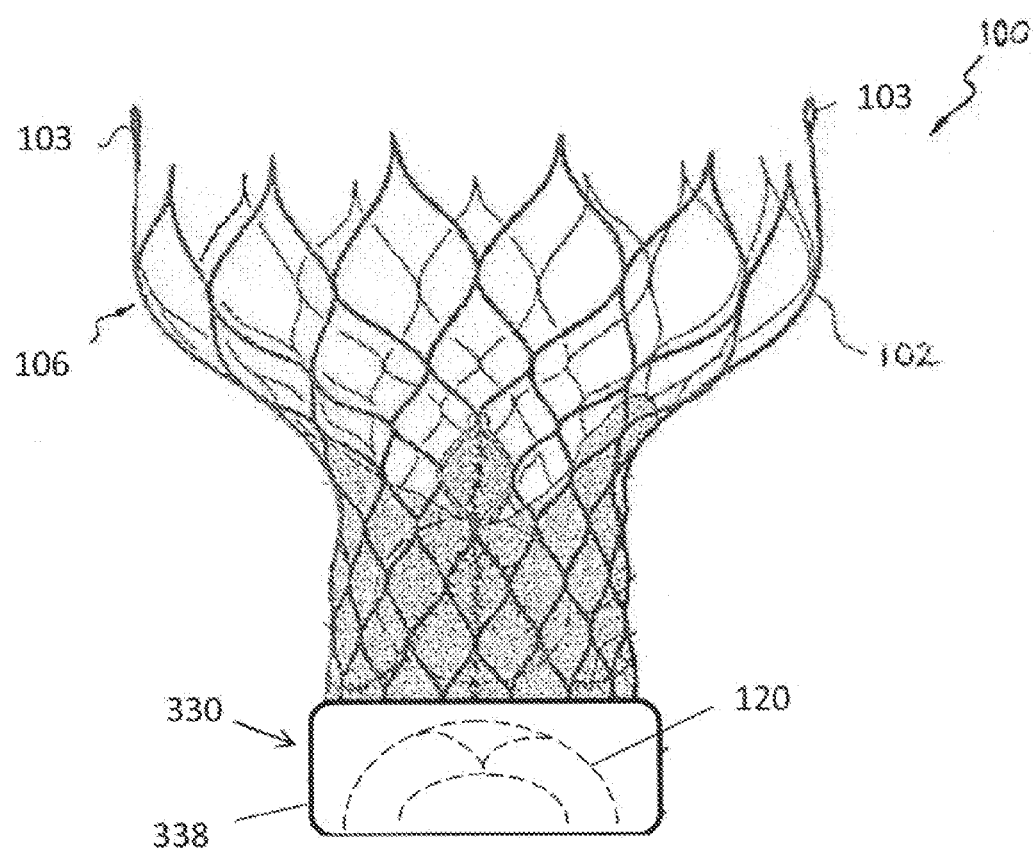
FIG. 30 is a side view illustration of a valve prosthesis for use in embodiments hereof.

Some embodiments hereof relate to methods for delivering a heart valve prosthesis having a self-expanding anti-paravalvular leakage component thereon that functions to occlude or fill gaps between the perimeter of a heart valve prosthesis and the native valve annulus, thereby reducing, minimizing, or eliminating leaks there through. An anti-paravalvular leakage component 330 is shown in FIG. 30 in its deployed or expanded configuration, extending around the outer surface or perimeter of stent 102 of heart valve prosthesis 100 adjacent to distal end 104 thereof to prevent paravalvular leakage in situ. When deployed, anti-paravalvular leakage component 330 may be positioned at the native valve annulus, slightly above the valve annulus, slightly below the valve annulus, or some combination thereof, and functions to substantially fill any/all gaps or cavities/crevices between the outer surface of stent 102 and native valve tissue. "Substantially fill" as utilized herein means that blood flow through the target gap or cavity is occluded or blocked, or stated another way blood is not permitted to flow there through. Anti-paravalvular leakage component 330 blocks blood flow around the outer perimeter of prosthesis 100, thereby minimizing and/or eliminating any paravalvular leakage at the implantation site. Although some embodiments depicted herein illustrate an anti-paravalvular leakage component integrated onto a heart valve prosthesis configured for implantation within an aortic valve, one of ordinary skill in the art would understand that an anti-paravalvular leakage component as described herein may be integrated onto a heart valve prosthesis configured for implantation within other heart valves such as but not limited to the mitral valve.

In one embodiment, anti-paravalvular leakage component 330 includes one or more elements 120 for sealing and one or more annular sealing members 338 coupled to the one or more elements 120. In one embodiment, annular sealing member 338 comprises one or more graft materials as described above. In one embodiment hereof elements 120 may be spaced apart in non-equal intervals or distances around the outside of the heart valve prosthesis 100. For example, it may be desirable to position one or more elements 120 at a location on the heart valve prosthesis corresponding to an area prone to leakage in situ, such as adjacent to the native valve commissures. In one embodiment, anti-paravalvular leakage component 330 is moveable between a compressed configuration and a deployed configuration.

In one embodiment, annular sealing skirt or member 338 is coupled to one or more elements 120. In one embodiment, annular sealing member 338 may be formed from a swellable material that collapses easily and expands to a larger volume after implantation, such as but not limited to hydrogel or a collagen foam/sponge similar to the material commercially available under the trademark Angioseal. Other suitable material examples for annular sealing member 338 include tissue, compressible foam materials, compressible polymeric materials, or a low-porosity knit or woven fabric, such as polyester, Dacron fabric, or PTFE. Porous materials advantageously provide a medium for tissue ingrowth and have the ability to stretch to conform to a curved surface. Polyester velour fabrics may alternatively be used, such as when it is desired to provide a medium for tissue ingrowth on one side and a smooth surface on the other side. Sealing member 338 may include one or more of the above-listed materials, such as but not limited to a combination of foam, fabric, and/or tissue.

In one embodiment, sealing member 338 is coupled to an inner surface of elements 120 when elements 120 are in the deployed configuration. Sealing member 338 may be coupled to elements 120 via sutures or other suitable mechanical connection. In another embodiment hereof sealing member 338 may be coupled to an outer surface of elements 120 when elements 120 are in the deployed configuration. In yet another embodiment hereof a first sealing member may be coupled to an inner surface of elements 120 and a second sealing member may be coupled to an outer surface of elements 120, thereby sandwiching elements 120 between two layers of sealing material.

In one embodiment, the length or diameter of sealing member 338 is approximately equal to or only slightly greater, for example, up to 10% greater, than the expanded outer diameter of stent 102. When elements 120 radially expand or deploy as described in more detail herein, annular sealing member 338 is positioned around the outer surface or perimeter of heart valve prosthesis 100. When deployed, annular sealing member 338 extends into and substantially fills any/all gaps or cavities/crevices between the outer surface of stent 102 and native valve tissue to prevent paravalvular leakage. In another embodiment hereof the length or diameter of sealing member 338 is between 10% and 50% greater than the expanded outer diameter of stent 102. As such, the material of sealing member 338 may bunch or billow in regions between adjacent elements 120. The excess or slack material may further extend into and substantially fill any/all gaps or cavities/crevices between the outer surface of stent 102 and native valve tissue to prevent paravalvular leakage in situ.

In one embodiment, sealing members 338 may be coupled or attached to one or more elements 120, wherein separate sealing members 338 together form a complete annular anti-paravalvular leakage component or seal 330. Alternatively, one or more sealing members 338 do not form a complete annular seal. In one embodiment, upon deployment of elements 120 in their deployed configuration, separate sealing members 338 coupled to each element 120 overlap to form a complete annular sealing member. In one embodiment, upon deployment of elements 120 in their deployed configuration, separate sealing members 338 coupled to each element 120 do not overlap to form a complete annular sealing member. Instead, sealing members 338 and elements 120 may be arranged around the perimeter of stent 102 so that in a deployed configuration sealing members 338 and elements 120 cover, surround, or extend around one or more portions of the surface or perimeter of stent 102, thereby not forming a complete annular sealing member. In one embodiment, prosthesis 100 may comprises different sized and shaped elements 120. For example, prosthesis 100 may comprise one or more elements 120 sized and shaped to serve as a sealing element and one or more elements 120 sized and shaped to serve as a positioning and/or anchoring element.

Deployment of anti-paravalvular leakage component 330 from the compressed or delivery configuration to the expanded or deployed configuration will now be discussed with reference to FIGS. 31-35. FIGS. 31-35 illustrate one embodiment of a progressive deployment of an anti-paravalvular leakage component 330 having annular sealing member 338 coupled to elements 120. Although not shown in FIGS. 31-35, in one embodiment, annular sealing member 338 may pack or compress within and between compressed elements 120 during delivery thereof. Accordingly, anti-paravalvular leakage component 330 advantageously does not increase, or minimally increases, the packing profile of heart valve prosthesis 100 so that heart valve prosthesis 100 has the ability to pack in lower profile delivery systems.

FIGS. 31-35 illustrate side and end views, respectively, of one embodiment of a progressive deployment of a valve prosthesis 100 in an compressed or delivery configuration sized for delivery to the target site, loaded into a delivery system 730. Valve prosthesis 100 includes a tubular frame or stent 102, a valve (not shown in FIGS. 31-35 for illustrative purposes) attached within the interior portion of stent 102, two elements 120 and a sealing membrane 338 coupled to elements 120. In the compressed or delivery configuration, each element 120 is approximately parallel with a longitudinal axis $L_a$ of stent 102 and distally extends from a distal end 104 of stent 102. Delivery system 730 includes a catheter 732 and an outer retractable sheath or tube 734. Valve prosthesis 100 is mounted over an inner shaft 736 of catheter 732 at the distal end thereof and sheath 734 surrounds and constrains valve prosthesis 100 in the compressed configuration. In one embodiment, catheter 732 may also include a retainer 738 which temporarily secures proximal end 706 of stent 702 onto catheter 732. For example, retainer 738 may include an end stent capture configuration as described in U.S. Patent Pub. 2009/0276027 to Glynn, which is hereby incorporated by reference herein in its entirety.

Figure 31:
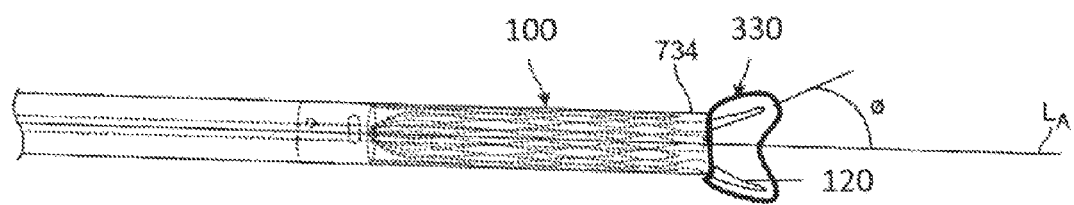
FIGS. 31-35 illustrate side views of the valve prosthesis of FIG. 30, wherein a sheath of a delivery system is progressively retracted to expose a sealing component of the valve prosthesis.
Figure 32:
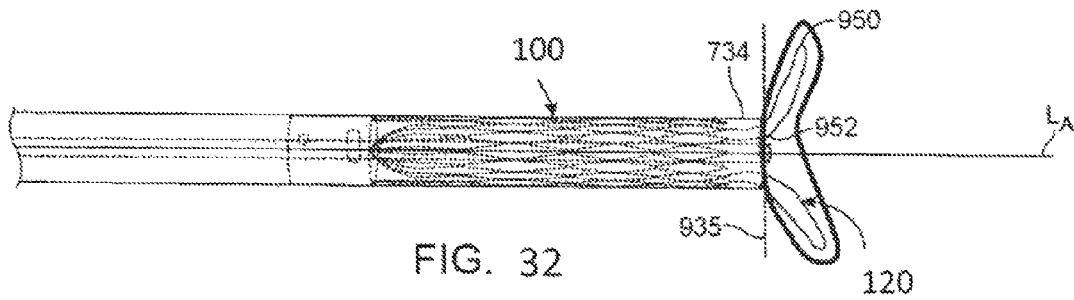
Figure 33:
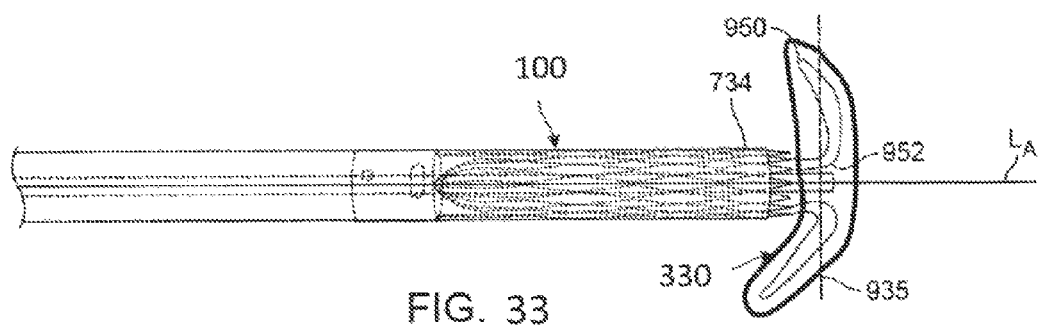

In order to begin deployment of valve prosthesis 100, sheath 734 is retracted in a proximal direction to expose and release elements 120 as shown in FIG. 31. Upon initial release from sheath 734, elements 120 flare or spread outwardly from the distal end of stent 102 such that elements 120 form an acute angle Ø with respect to longitudinal axis $L_a$. Sealing member 338 radially expands or bulges outward when elements 120 are released from sheath 734. As sheath 734 is further retracted, elements 120 continue to be exposed and continue to bend backwards towards the outer surface of sheath 734 and stent 102. Notably, as elements 120 are released from sheath 734, stent 102 remains constrained within sheath 734. FIG. 32 illustrates elements 120 approaching a transverse reference axis 935 between the initial distally-extending compressed configuration and the final proximally-extending deployed configuration. Transverse reference axis 935 as utilized herein describes an imaginary reference line that extends approximately ninety degrees or perpendicular to the longitudinal axis La of stent 702. FIG. 33 illustrates elements 120 after passing over the transverse reference axis 935, with elements 120 fully exposed or released from sheath 734 while stent 102 is still compressed within sheath 734. One particular feature of elements 120 is apparent when comparing FIG. 32 and FIG. 33. Elements 120 bend or curve gradually backwards such that distal portions or tips 950 of elements 120 pass over the transverse reference axis 935 before proximal portions or bases 952 of elements 120. After distal tips 950 of elements 120 pass or cross over the transverse reference axis 935 and are pointing in a proximal direction, proximal bases 952 of elements 120 approach the transverse reference axis 935 as shown in FIG. 33. Stated another way, distal tips 950 of each element 120 bend past transverse reference axis 935 prior to proximal bases 952 of each element 120. Due to the above-described flaring or expanding sequence in which elements 120 curve backward, the length of elements 120 may be greater than if both the proximal and distal portions of elements 120 crossed over the transverse reference axis 935 at the same time, i.e., if elements 120 were straight and extended generally parallel to the transverse reference axis 935 during deployment. In addition, since stent 102 is still compressed within sheath 734, it can be observed that the length of elements 120 may be greater than if stent 102 was released from sheath 734 and in a deployed configuration.

Figure 34:
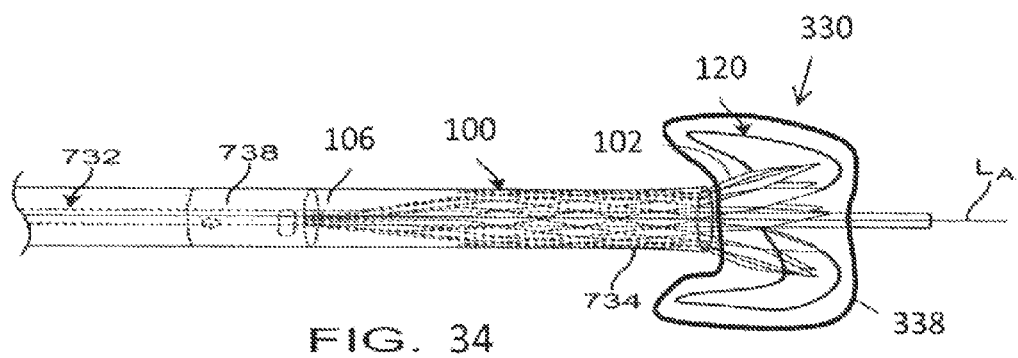
Figure 35:
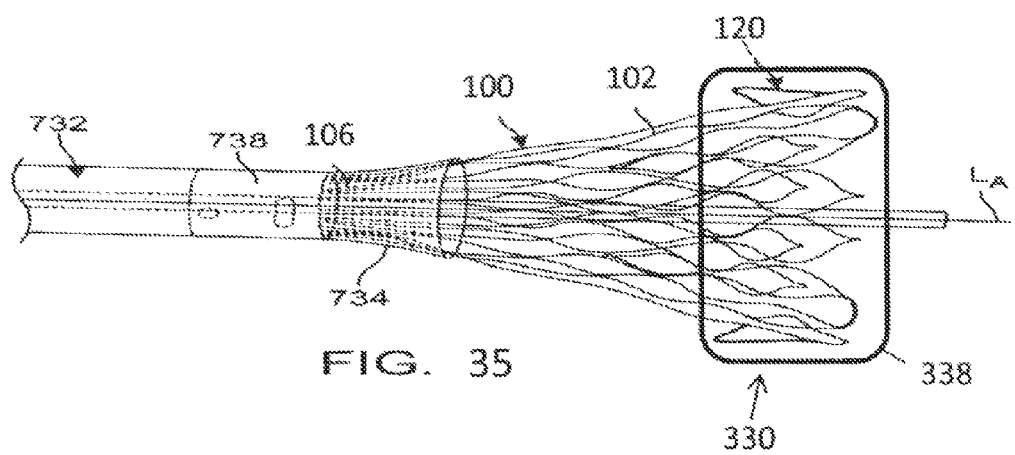

FIG. 34 and FIG. 35 illustrate the continued deployment of valve prosthesis 100. Sheath 734 continues to be proximally retracted, exposing self-expanding stent 102 such that stent 102 is released to assume its deployed configuration. Sheath 734 is proximally retracted until proximal end 106 of stent 102 is exposed and allowed to self-expand, thereby uncoupling from retaining tip 738 of catheter 732. As sheath 734 was retracted, anti-paravalvular leakage component 330 continued to be exposed and elements 120 continued to bend backwards towards the outer surface of sheath 734 and stent 102.

Figure 36:
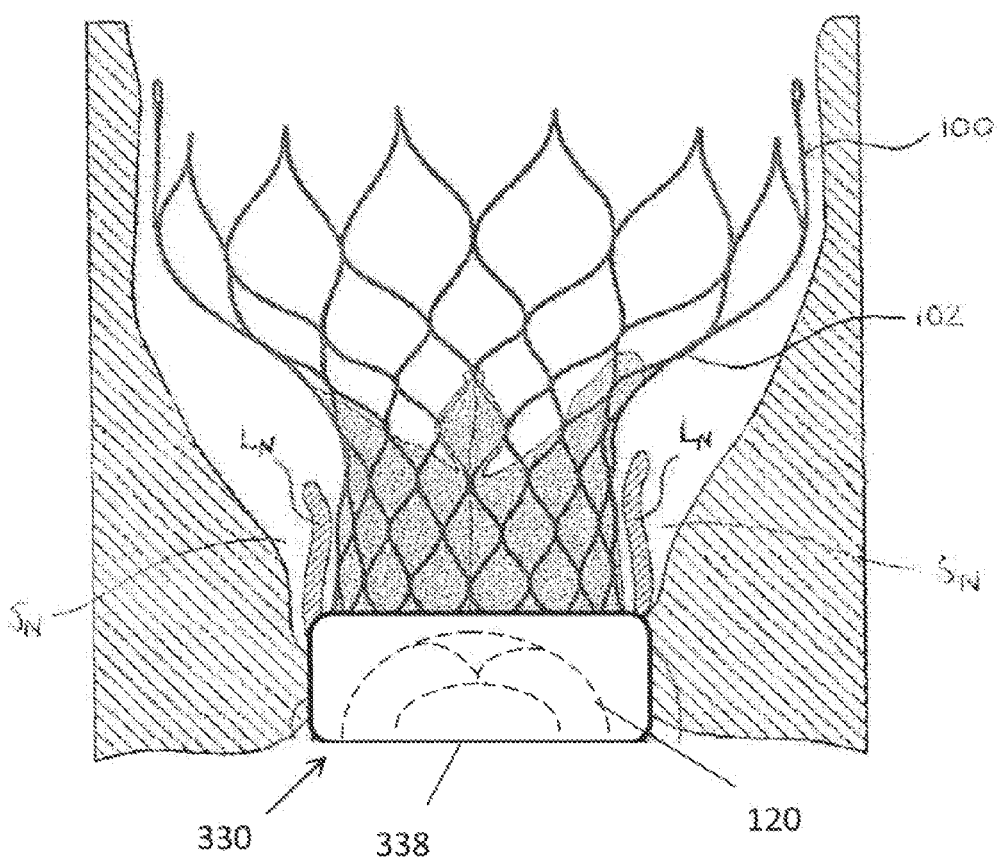
FIG. 36 illustrates a side view of the valve prosthesis of FIG. 30 in an expanded or deployed configuration, after release from a delivery system and implanted within a native valve annulus.

FIG. 36 illustrates the final deployed configuration of valve prosthesis 100, in which each element 120 proximally extends from a distal end 104 of stent 102. In this embodiment, sealing member 338 is shown extending between elements 120 and extending into and substantially filling any/all gaps or cavities/crevices between outer surface of stent 102 and native valve tissue to prevent paravalvular leakage in situ. As previously described, the backwards rotation that occurs during deployment results in each element 120 translating more than ninety degrees from its compressed, delivery configuration. During deployment, each element 120 essentially deploys or translates in an arc path that extends between 90 and 180 degrees from the initial compressed configuration and the final deployed configuration. In the embodiment of FIG. 36 shown ex vivo, each element 120 bent or rotated about 180 degrees between the initial distally-extending compressed configuration and the final proximally-extending deployed configuration. In one embodiment, when positioned in vivo, one or more sealing members 338 may be sandwiched between one or more elements 120 and the outer surface of stent 102 and as a result, the total rotation or bending of elements 120 in the final deployed configuration may be less than 180 degrees with respect to the initial distally-extending compressed configuration.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. For example, although support arms of various embodiments are described herein as U-shaped, it will be understood by one of ordinary skill in the art that any support arm described herein may be generally U-shaped or V-shaped as shown in FIGS. 26A-26F. In addition, valve prostheses described here may include one or more elements for positioning and/or sealing that transform from either an initial distally-extending compressed configuration to a final proximally-extending deployed configuration, or an initial proximally-extending compressed configuration to a final distally-extending deployed configuration, or both. In one embodiment, a minimum of two elements for positioning and/or sealing are employed such that a support arm is positioned behind each leaflet of a native mitral valve. However, additional elements for positioning and/or sealing may be included without departing from the spirit and scope of the invention. In one embodiment, four elements for positioning and/or sealing may be circumferentially disposed around the perimeter of a stent that supports a prosthetic bileaflet valve therein. In another embodiment, three elements for positioning and/or sealing may be circumferentially disposed around the perimeter of a stent that supports a prosthetic trileaflet valve therein.

In addition to variations of the elements for positioning and/or sealing, various changes in form and detail can be made to the stent of the valve prosthesis without departing from the spirit and scope of the invention. As previously described, the stent frame may have any suitable configuration known in the art. In addition, although not required, portions of the stent may be selectively plated with platinum or other biocompatible material to provide improved visibility during fluoroscopy and thereby aid in positioning the stent in the middle of the mitral valve for deployment. In one embodiment of the present invention, one or more radiopaque markers (not shown) may be attached to the valve prosthesis at one or more predetermined locations. The marker may be formed of platinum or any other relatively heavy metal, which may be generally visible by X-ray fluoroscopy.

Accordingly, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A heart valve prosthesis comprising:
   a tubular stent having a compressed configuration for delivery within a vasculature and a deployed configuration for deployment within a native heart valve;
   a prosthetic valve component disposed within and secured to the stent;
   one or more elements coupled to a distal end of the stent, each element including an outer generally U-shaped or V-shaped support arm and an inner generally V-shaped or U-shaped support arm that both distally extend from the distal end of the stent when the stent is in the compressed configuration, each generally U-shaped or V-shaped support arm having a first end and a second end coupled to the distal end of the stent with a peak formed between the first and second ends, the outer and inner support arms extending along the same plane and the inner support arm being disposed within the outer support arm such that the peaks of the inner and outer support arms are aligned, and such that each of the first and second ends of the outer support arm is coupled to the stent at a circumferentially spaced apart location from the respective first and second ends of the inner support arm, wherein during deployment of the prosthesis each support arm bends radially outward and then towards an outer surface of the stent such that it translates more than ninety degrees from the compressed configuration to proximally extend from the distal end of the stent when the stent is in the deployed configuration; and a graft material coupled to at least a portion of the heart valve prosthesis.

2. The heart valve prosthesis of claim 1, wherein each element is approximately parallel with a longitudinal axis of the stent and distally extends from the distal end of the stent when the stent is in the compressed configuration.

3. The heart valve prosthesis of claim 2, wherein each element rotates in a radial direction between 135 degrees and 180 degrees from the compressed configuration during deployment of the prosthesis.

4. The heart valve prosthesis of claim 1, wherein the graft material is coupled to at least a portion of the tubular stent.

5. The heart valve prosthesis of claim 1, wherein the graft material is coupled to the one or more elements.

6. The heart valve prosthesis of claim 1, wherein the stent and the elements are formed as a unitary structure.

7. The heart valve prosthesis of claim 1, wherein a connector extends from the peak of the outer support arm to the peak of the inner support arm and couples the peaks of the support arms together to ensure that the support arms remain in the same plane during deployment of the prosthesis, the connector including two curved legs, wherein first ends of the curved legs extend from the peak of the inner support arm and the curved legs flare away from each other such that second ends of the legs extend from opposing sides of the peak of the outer support arm.

8. The heart valve prosthesis of claim 1, wherein each support arm extends from distalmost crowns of the stent.

9. The heart valve prosthesis of claim 1, wherein each support arm extends from between distalmost crowns of the stent.

10. The heart valve prosthesis of claim 1, wherein each element includes an intermediate U-shaped or V-shaped support arm between the outer support arm and the inner support arm, the intermediate support arm having a first end and a second end coupled to the distal end of the stent with a peak formed between the first and second ends.

11. A heart valve prosthesis comprising:

a tubular stent having a compressed configuration for delivery within a vasculature and a deployed configuration for deployment within a native heart valve;

a prosthetic valve component disposed within and secured to the stent; and one or more elements coupled to a distal end of the stent, each element including an outer support arm having a first end and a second end coupled to the distal end of the stent with a peak formed between the first and second ends and an inner support arm having a first end and a second end coupled to the distal end of the stent with a peak formed between the first and second ends, the outer and inner support arms extending along the same plane and the inner support arm being disposed within the outer support arm such that the peaks of the inner and outer support arms are aligned and each of the first and second ends of the outer support arm is coupled to the stent at a circumferentially spaced apart location from the respective first and second ends of the inner support arm, wherein during deployment of the prosthesis each support arm bends radially outward and then towards an outer surface of the stent such that it translates more than ninety degrees from the compressed configuration to the deployed configuration; and at least one sealing member coupled to the one or more elements, wherein the sealing member is positioned around an outer surface of the tubular stent when the tubular stent is in the deployed configuration.

12. The heart valve prosthesis of claim 11, wherein each element distally extends from the distal end of the stent when the stent is in the compressed configuration and proximally extends from the distal end of the stent when the stent is in the deployed configuration.

13. The heart valve prosthesis of claim 11, wherein each element proximally extends from the proximal end of the stent when the stent is in the compressed configuration and distally extends from the proximal end of the stent when the stent is in the deployed configuration.

14. The heart valve prosthesis of claim 11, wherein graft material is coupled to at least a portion of the tubular stent.

15. The heart valve prosthesis of claim 11, wherein the at least one sealing member is coupled to an inner surface of the one or more elements when the elements are in the deployed configuration.

16. The heart valve prosthesis of claim 11, wherein the at least one sealing member is coupled to an outer surface of the one or more elements when the elements are in the deployed configuration.

17. The heart valve prosthesis of claim 11, wherein the at least one sealing member includes a first sealing member and a second sealing member, the first sealing member being coupled to an inner surface of the one or more elements when the elements are in the deployed configuration and the second sealing member being coupled to an outer surface of the one or more elements when the elements are in the deployed configuration.

18. The heart valve prosthesis of claim 11, wherein the sealing member is annular and a diameter of the sealing member is no more than 10% greater than an outer diameter of the tubular stent in the deployed configuration.

19. The heart valve prosthesis of claim 11, wherein the sealing member is annular and a diameter of the sealing member is between 10% and 50% greater than an outer diameter of the tubular stent in the deployed configuration.

20. The heart valve prosthesis of claim 11, wherein the at least one sealing member includes a plurality of separate sealing members that collectively form a complete annular seal.

* * * * *